(12) United States Patent
Patton et al.

(10) Patent No.: US 7,384,545 B2
(45) Date of Patent: *Jun. 10, 2008

(54) CONTAINER FOR INHIBITING MICROBIAL GROWTH IN LIQUID NUTRIENTS

(75) Inventors: David L. Patton, Webster, NY (US); Joseph F. Bringley, Rochester, NY (US); Richard W. Wien, Pittsford, NY (US); John M. Pochan, Penfield, NY (US); Yannick J. F. Lerat, Mellecey (FR); William J. Harrison, Pittsford, NY (US)

(73) Assignee: Eastman Kodak Company, Rochester, NY (US)

( * ) Notice: Subject to any disclaimer, the term of this patent is extended or adjusted under 35 U.S.C. 154(b) by 239 days.

This patent is subject to a terminal disclaimer.

(21) Appl. No.: 10/985,377

(22) Filed: Nov. 10, 2004

(65) Prior Publication Data

US 2005/0224425 A1 Oct. 13, 2005

Related U.S. Application Data

(63) Continuation-in-part of application No. 10/936,929, filed on Sep. 9, 2004, which is a continuation-in-part of application No. 10/823,446, filed on Apr. 13, 2004.

(51) Int. Cl.
*B01D 57/00* (2006.01)
*B65D 23/02* (2006.01)
(52) U.S. Cl. .............. 210/198.1; 206/524.3; 206/524.4; 210/209; 215/12.1; 220/61.12; 264/255; 264/259; 264/513; 426/271; 426/322; 426/326; 426/330.3; 428/35.7; 428/323

(58) Field of Classification Search ............. 210/198.1
See application file for complete search history.

(56) References Cited

U.S. PATENT DOCUMENTS

| 4,965,084 A | | 10/1990 | Austin et al. |
| 5,035,931 A | * | 7/1991 | Yamada et al. ............. 428/35.7 |
| 5,049,280 A | | 9/1991 | Raymond et al. |
| 5,710,190 A | * | 1/1998 | Jane et al. .................. 521/102 |
| 5,854,303 A | | 12/1998 | Powell et al. |

(Continued)

FOREIGN PATENT DOCUMENTS

FR 2 772 019 6/1999

(Continued)

OTHER PUBLICATIONS

"Active Packaging of Food Applications" by Aaron L. Brody et al., Technomic Publishing Company, Inc. Pennsylvania (2001).

*Primary Examiner*—Peter A. Hruskoci
(74) *Attorney, Agent, or Firm*—Frank Pincelli; Eugene I. Shkurko

(57) ABSTRACT

A fluid container and method for inhibiting the growth of microbes in liquid nutrient in a container, the container having an interior surface having a metal-ion sequestering agent and/or antimicrobial agent provided in a localized area of the container formed by a two shot molding, insert molding or two shot injection stretch blow molding process, said metal ion sequestering agent provided for the removing and/or inhibiting growth of microbes in the liquid nutrient.

38 Claims, 21 Drawing Sheets

U.S. PATENT DOCUMENTS

| | | | |
|---|---|---|---|
| 6,063,465 A * | 5/2000 | Charbonneau et al. ... | 428/36.92 |
| 6,132,750 A | 10/2000 | Perrier et al. | |
| 6,426,128 B1 * | 7/2002 | Kimmel et al. ............. | 428/1.6 |
| 6,465,065 B1 * | 10/2002 | Teumac et al. ............ | 428/35.7 |
| 6,548,264 B1 * | 4/2003 | Tan et al. ................. | 435/7.21 |
| 6,610,763 B1 * | 8/2003 | Beese ....................... | 523/122 |
| 6,641,842 B2 * | 11/2003 | Laridon et al. ............ | 424/486 |
| 6,667,082 B2 * | 12/2003 | Bamore et al. ............ | 428/34.8 |
| 6,838,186 B2 * | 1/2005 | Aral et al. .................. | 428/516 |
| 6,933,046 B1 * | 8/2005 | Cook ......................... | 428/402 |
| 7,258,786 B2 * | 8/2007 | Patton et al. ............. | 210/198.1 |
| 7,258,787 B2 * | 8/2007 | Patton et al. ............. | 210/198.1 |
| 2002/0000289 A1 | 1/2002 | Nickell et al. | |

FOREIGN PATENT DOCUMENTS

| | | |
|---|---|---|
| WO | WO 03/088914 | 10/2003 |

\* cited by examiner

CONTAINER FOR INHIBITING MICROBIAL GROWTH IN LIQUID NUTRIENTS

CROSS REFERENCE TO RELATED APPLICATIONS

This is a Continuation-in-Part of U.S. patent application Ser. No. 10/936,929 filed Sep. 9, 2004 which is a Continuation-in-Part of application Ser. No. 10/823,446 filed Apr. 13, 2004.

Reference is also made to commonly assigned pending U.S. patent application Ser. No. 10/985,378 filed Nov. 10, 2004 entitled CONTAINER FOR INHIBITING MICROBIAL GROWTH IN LIQUID NUTRIENTS by David L. Patton, Joseph F. Bringley, Richard W. Wien, John M. Pochan, Yannick L. F. Lerat, Narasimharao Dontula and pending U.S. patent application Ser. No. 10/985,393 filed Nov. 10, 2004 entitled CONTAINER FOR INHIBITING MICROBIAL GROWTH IN LIQUID NUTRIENTS by David L. Patton, Joseph F. Bringley, Richard W. Wien, John M. Pochan, Yannick L. F. Lerat, Narasimharao Dontula the disclosures of which are incorporated herein by reference.

FIELD OF THE INVENTION

The present invention relates to a fluid container having a metal-ion sequestering agent for removing bio-essential metal ions from a liquid nutrient for inhibiting growth of microbes in the liquid nutrient.

BACKGROUND OF THE INVENTION

It has been recognized that small concentrations of metal ions play an important role in biological processes. For example, Mn, Mg, Fe, Ca, Zn, Cu and Al are essential bio-metals, and are required for most, if not all, living systems. Metal ions play a crucial role in oxygen transport in living systems, and regulate the function of genes and replication in many cellular systems. Calcium is an important structural element in the life of bacteria regulating enzyme activity. Mn, Cu and Fe are involved in metabolism and enzymatic processes. At high concentrations, metals may become toxic to living systems and the organism may experience disease or illness if the level cannot be controlled. As a result, the availability, and concentrations, of metal ions in biological environments is a major factor in determining the abundance, growth-rate and health of plant, animal and micro-organism populations.

It has also been recognized that iron is an essential biological element, and that all living organisms require iron for survival and replication. Although, the occurrence and concentration of iron is relatively high on the earth's surface, the availability of "free" iron is severely limited by the extreme insolubility of iron in aqueous environments. As a result, many organisms have developed complex methods of procuring "free" iron for survival and replication.

Articles, such as food and beverage containers are needed that are able to improve food quality, to increase shelf-life, to protect from microbial contamination, and to do so in a manner that is safe for the user of such items and that is environmentally clean while providing for the general safety and health of the public. Materials and methods are needed to prepare articles having antimicrobial properties that are less, or not, susceptible to microbial resistance. Methods are needed that are able to target and remove specific, biologically important, metal ions while leaving intact the concentrations of beneficial metal ions.

During the process of filling containers with certain beverages and foods, air borne pathogens enter the containers after the flash pasteurization or pasteurization part of the process. These pathogens such as yeast, spores, bacteria, etc. will grow in the nutrient rich beverage or food, ruining the taste or even causing hazardous microbiological contamination. While some beverages are packaged by aseptic means or by utilizing preservatives, many other beverages, for example fruit juices, teas and isotonic drinks are "hot-filled". "Hot-filling" involves the filling of a container with a liquid beverage having some elevated temperature (typically, at about 180-200° F.). The container is capped and allowed to cool, producing a partial vacuum therein. The process of hot filling of beverages and foods is used to kill the pathogens, which enter the container during the filling of the beverage or food containers. Hot filling requires containers be made of certain materials or constructed in a certain fashion such as thicker walls to withstand the hot filling process. The energy required for hot filling adds to the cost of the filling process. Temperatures required for hot filling have a detrimental effect on the flavor of the beverage. Other methods of filling such as aseptic filling require large capital expenditures and maintaining class 5 clean room conditions.

U.S. Pat. No. 5,854,303 discloses a polymeric material incorporating a polyvalent cation chelating agent in an amount effective to inhibit the growth of a protozoan on the surface of contact lenses and in other eye care products.

PROBLEM TO BE SOLVED BY THE INVENTION

The present invention is directed to the problem of the growth of micro-organism in liquids provided in containers that adversely affects food quality, shelf-life, to protect from microbial contamination, and to do so in a manner that is safe for the user of such and a method for efficient fabrication of the container and for controlling the location of the active material for providing such protection.

SUMMARY OF THE INVENTION

In accordance with one aspect of the present invention, there is provided a fluid container for containing a liquid nutrient having a pH equal to or greater than about 2.5, the container having an interior surface having a metal-ion sequestering agent provided in a localized area of the container formed by a two shot molding, insert molding or two shot injection stretch blow molding process, the metal ion sequestering agent provided for the removing of a designated metal ion from the liquid nutrient for inhibiting growth of microbes in the liquid nutrient and/or an antimicrobial agent for reducing and/or maintaining the amount of microbes in the liquid nutrient to a prescribed condition.

In accordance with another aspect of the present invention there is provided a method for inhibiting growth of microbes in a liquid, comprising the steps of:

a. providing a container for holding a liquid having a pH equal to or greater than about 2.5, the container having an internal surface having an ion sequestering agent provided in a localized area of the container formed by a two shot molding, insert molding or two shot injection stretch blow molding process, the metal ion sequestering agent provided for the removing of designated metal ions from the liquid and/or an antimicrobial agent for reducing and/or maintaining the amount of microbes in the liquid nutrient to a prescribed condition;

b. filling the container with the liquid in an open environment;

c. closing the container with the liquid contained therein; and c. shipping the container for use of the liquid without any further processing of the container containing the liquid.

In accordance with still another aspect of the present invention there is provided an article for inhibiting the growth of microbes in a liquid nutrient when placed in contact with the liquid nutrient, the article having a metal ion sequestering agent and/or an antimicrobial agent provided in a localized area of the container formed by a two shot molding, insert molding or two shot injection stretch blow molding process, the metal ion sequestering agent and/or the antimicrobial agent are provided for the removing of such that when the article is placed in contact with the liquid nutrient the metal-ion sequestering agent and the antimicrobial agents inhibit the growth of microbes in the liquid nutrient, the metal-ion sequestering agent comprising derivatized nanoparticles.

These and other aspects, objects, features and advantages of the present invention will be more clearly understood and appreciated from a review of the following detailed description of the preferred embodiments and appended claims and by reference to the accompanying drawings.

BRIEF DESCRIPTION OF THE DRAWINGS

In the detailed description of the preferred embodiments of the invention presented below, reference is made to the accompanying drawings in which.

DETAILED DESCRIPTION OF THE INVENTION

Figure 1:
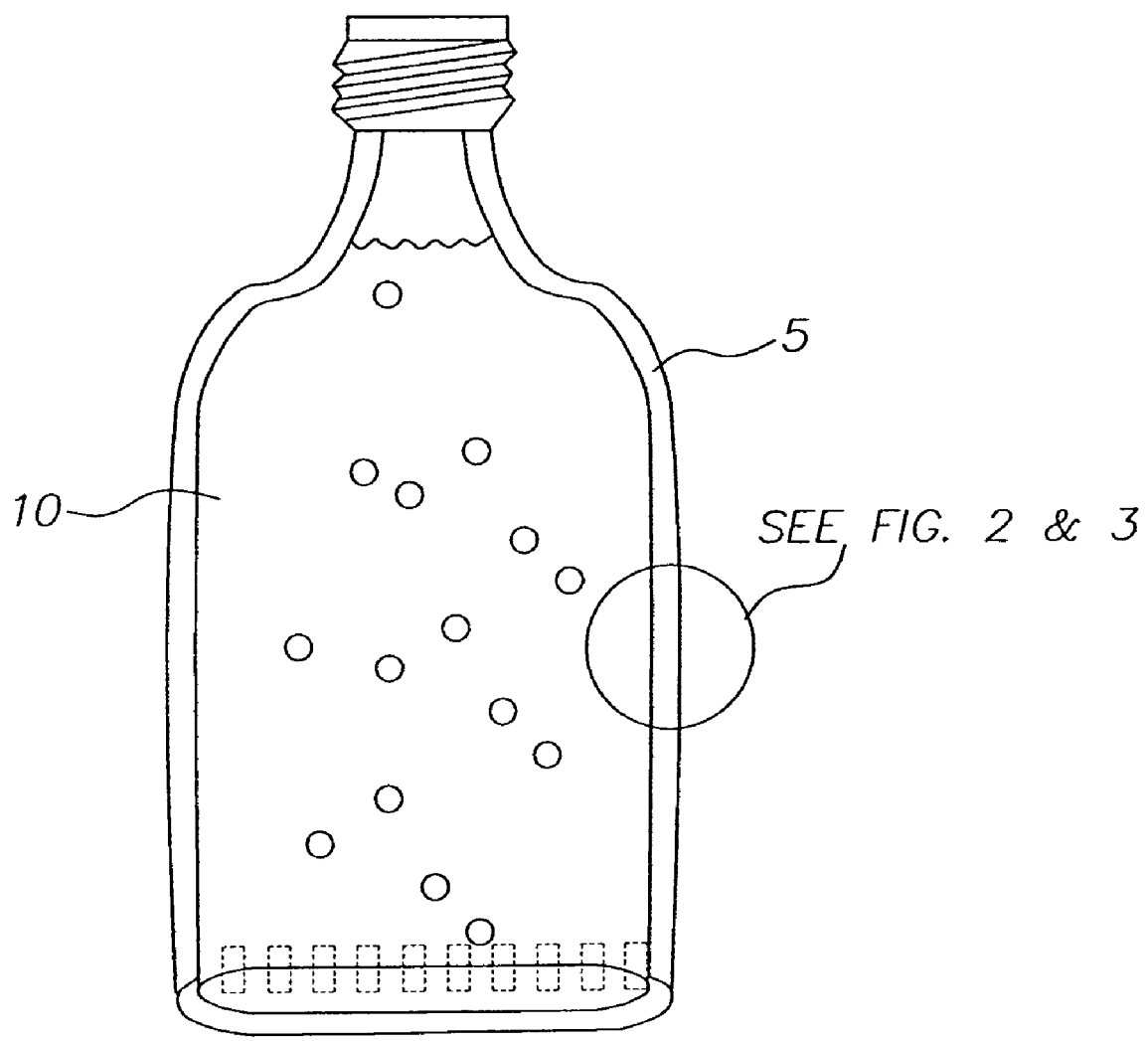
FIG. 1 illustrates a cross section of a fluid container made in accordance with the prior art.

The growth of microbes in an article such as a fluid container containing a liquid nutrient comprising a liquid nutrient can be inhibited by placing metal-ion sequestering agents, as described in U.S. patent application Ser. No. 10/822,940 filed Apr. 13, 2004 entitled DERIVATIZED NANOPARTICLE COMPRISING METAL-ION SEQUESTRANT by Joseph F. Bringley, and U.S. patent application Ser. No. 10/822,929 filed Apr. 13, 2004 entitled COMPOSITION OF MATTER COMPRISING POLYMER AND DERIVATIZED NANOPARTICLES by Joseph F. Bringley et al. capable of removing a designated metal ion for example, Mn, Mg, Fe, Ca, Zn, Cu and Al from said liquid nutrients, in contact with the nutrient. Intimate contact is achieved by incorporating the metal-ion sequestering agent as an integral part of the support structure of the article. For example, one can control the concentration of "free" iron in the liquid nutrient held by the article by placing an iron sequestering agent in the walls of the container, which in turn controls the growth rates, and abundance of microorganisms. The articles of the invention further contain an effective amount of an antimicrobial agent, which quickly reduces the population of microbes to a manageable level, and insures the effectiveness of metal-ion sequestering or binding agents. The invention "starves" the remaining micro-organisms of minute quantities of essential nutrients (metal-ions) and hence limits their growth and reduces the risk due to bacterial, viral and other infectious diseases. The article, such as a container, may be used for holding a food or beverage.

The term inhibition of microbial-growth, or a material which "inhibits" microbial growth, is used by the authors to mean materials which either prevent microbial growth, or subsequently kills microbes so that the population is within acceptable limits, or materials which significantly retard the growth processes of microbes or maintain the level or microbes to a prescribed level or range. The prescribed level may vary widely depending upon the microbe and its pathogenicity; generally it is preferred that harmful organisms are present at no more than 10 organisms/ml and preferably less than 1 organism/ml. Antimicrobial agents which kill microbes or substantially reduce the population of microbes are often referred to as biocidal materials, while materials which simply slow or retard normal biological growth are referred to as biostatic materials. The preferred impact upon the microbial population may vary widely depending upon the application, for pathogenic organisms (such as E. coli O157:H7) a biocidal effect is more preferred, while for less harmful organisms a biostatic impact may be preferred. Generally, it is preferred that microbiological organisms remain at a level which is not harmful to the consumer or user of that particular article Metal-ion sequestering agents may be incorporated into articles by placing the metal-ion sequestering agents on the surface of the article, or by putting the metal-ion sequestering agents within the materials used to form the article. In all instances, the metal-ion sequestering agents must be capable of contacting the food or beverage held by the container.

Figure 2:
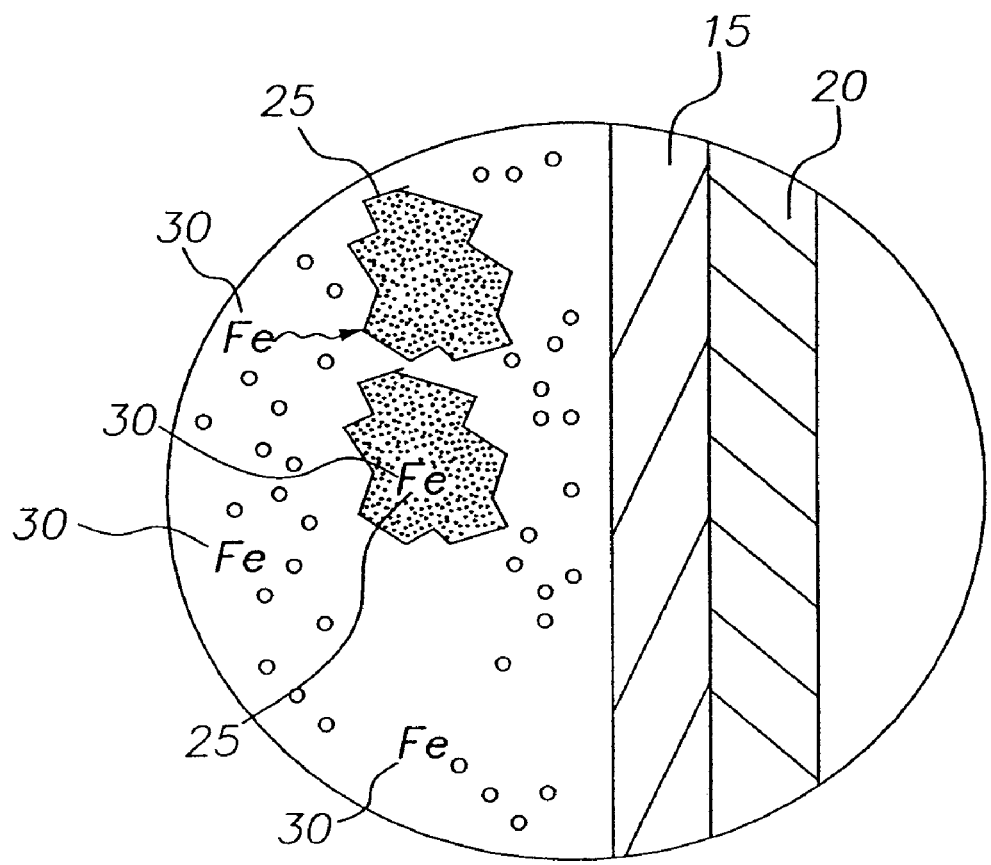
FIG. 2 is an enlarged partial cross sectional view of a portion of the container of FIG. 1 illustrating a "free" iron ion sequestering agent.

Referring to FIG. 1, there is illustrated a cross-sectional view of a typical prior art container. In the embodiment illustrated, the container comprises a bottle 5 holding a liquid nutrient 10, for example an isotonic liquid. Drinks such as Gatorade™ or PowerAde™ are examples of isotonic drinks/liquids. The container 5 may be made of one or more layers of a plastic polymer using various molding processes known by those skilled in the art. Examples of polymers used in the manufacture of bottles are PET (polyethylene terephthalate), PP (polypropylene), LDPE (low density polyethylene) and HDPE (high density polyethylene). FIG. 2 illustrates a plastic bottle 5 formed using two different polymeric layers 15 and 20. However it is to be understood that the container 5 may comprise any desired number of layers.

A fluid container made in accordance with the present invention is especially useful for containing a liquid nutrient having a pH equal to or greater than about 2.5. The container is designed to have an interior surface having a metal-ion sequestering agent for removing a designated metal ion from a liquid nutrient for inhibiting growth of microbes in said liquid nutrient. It is preferred that the metal-ion sequestrant is immobilized within the materials forming the container or is immobilized within a polymeric layer directly in contact with the beverage or liquid nutrient. It is further preferred that the metal-ion sequestering agent is immobilized on the surface(s) of said container. This is important because metal-ion sequestrants that are not immobilized may diffuse through the material or polymeric layers of the container and dissolve into the contents of the beverage. Metal ions complexed by dissolved sequestrants will not be sequestered within the surfaces of the container but may be available for use by micro-organisms.

It is preferred that the sequestering agent is immobilized on the surface(s) of said container and has a high-affinity for biologically important metal ions such as Mn, Mg, Zn, Cu and Fe. It is further preferred that the immobilized sequestering agent has a high-selectivity for biologically important metal ions such as Mn, Mg, Zn, Cu and Fe. It is preferred that said sequestering agent has a high-selectively for certain metal ions but a low-affinity for at least one other ion. It is further preferred that said certain metal ions comprises Mn, Mg, Zn, Cu and Fe and said other at least one ion comprises calcium. This is preferred because some metal ions such as calcium, sodium and potassium may be beneficial to the taste and quality of the food, and are usually very highly abundant in foodstuffs and in liquid extrudates of foodstuffs. It is preferred that said metal-ion sequestering agent is immobilized on the surface(s) of said container and has a stability constant greater than $10^{10}$ with iron (III), more preferably greater than $10^{20}$ with iron (III), and most preferably greater than $10^{30}$ with iron (III). This is preferred because iron is an essential nutrient for virtually all micro-organisms, and sequestration of iron may most beneficially limit the growth of micro-organisms.

In a particularly preferred embodiment, the invention provides a fluid container wherein said metal-ion sequestering agent comprises derivatized nanoparticles comprising inorganic nanoparticles having an attached metal-ion sequestrant, wherein said inorganic nanoparticles have an average particle size of less than 200 nm and the derivatized nanoparticles have a stability constant greater than $10^{10}$ with iron (III). It is preferred that the inorganic nanoparticles have an average particle size of less than 100 nm. It is preferred that said metal-ion sequestrant is attached to the nanoparticle by reacting the nanoparticle with a silicon alkoxide intermediate of the sequestrant having the general formula:

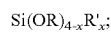

$$Si(OR)_{4-x}R'_x;$$

wherein x is an integer from 1 to 3;

R is an alkyl group; and

R' is an organic group containing an alpha amino carboxylate, a hydroxamate, or a catechol. Derivatized nanoparticles useful for practice of the invention are described in detail in U.S. patent application Ser. No. 10/822,940 filed Apr. 13, 2004 entitled DERIVATIZED NANOPARTICLE COMPRISING METAL-ION SEQUESTRAINT by Joseph F. Bringley.

In a preferred embodiment the metal-ion sequestering agent is immobilized in a polymeric layer, and the polymeric layer contacts the fluid contained therein. The metal-ion sequestrant may be formed integrally within the materials comprising the bottle or may be contained within a polymeric layer directly in contact with the beverage or liquid nutrient. It is preferred that the polymer is permeable to water. It is preferred that the metal-ion sequestering agent comprises are 0.1 to 50.0% by weight of the polymer. Polymers useful for practice of the invention are described in detail in U.S. patent application Ser. No. 10/823,453 filed Apr. 13, 2004 entitled ARTICLE FOR INHIBITING MICROBIAL GROWTH by Joseph F. Bringley et al.

In a preferred embodiment, the metal-ion sequestering agent comprises an alpha amino carboxylate, a hydroxamate, or a catechol functional group. Metal-ion sequestrants suitable for practice of the invention include ethylenediaminetetraacetic acid (EDTA), ethylenediaminetetraacetic acid disodium salt, diethylenetriaminepentaacetic acid (DTPA), Hydroxylpropylenediaminetetraacetic acid (DPTA), nitrilotriacetic acid, triethylenetetraaminehexaacetic acid, N,N'-bis(o-hydroxybenzyl) ethylenediamine-N,N' diacteic acid, and ethylenebis-N,N'-(2-o-hydroxyphenyl) glycine, acetohydroxamic acid, and desferroxamine B (the iron chelating drug desferal), catechol, disulfocatechol, dimethyl-2,3-dihydroxybenzamide, mesitylene catecholamide (MECAM) and derivatives thereof, 1,8-dihydroxynaphthalene-3,6-sulfonic acid, and 2,3-dihydroxynaphthalene-6-sulfonic acid, and siderophores molecules naturally synthesized by micro-organisms which have a very high affinity for Fe. Metal-ion sequestering agents suitable for use in the invention are described at length in U.S. patent application Ser. No. 10/822,940 filed Apr. 13, 2004 entitled DERIVATIZED NANOPARTICLE COMPRISING METAL-ION SEQUESTRANT by Joseph F. Bringley et al.

The antimicrobial active material of antimicrobial agent 5 may be selected from a wide range of known antibiotics and antimicrobials. An antimicrobial material may comprise an antimicrobial ion, molecule and/or compound, metal ion exchange materials exchanged or loaded with antimicrobial ions, molecules and/or compounds, ion exchange polymers and/or ion exchange latexes, exchanged or loaded with antimicrobial ions, molecules and/or compounds. Suitable materials are discussed in "Active Packaging of Food Applications" A. L. Brody, E. R. Strupinsky and L. R. Kline, Technomic Publishing Company, Inc. Pennsylvania (2001). Examples of antimicrobial agents suitable for practice of the invention include benzoic acid, sorbic acid, nisin, thymol, allicin, peroxides, imazalil, triclosan, benomyl, metal-ion release agents, metal colloids, anhydrides, and organic quaternary ammonium salts. Preferred antimicrobial reagents are metal ion exchange reagents such as silver sodium zirconium phosphate, silver zeolite, or silver ion exchange resin which are commercially available. The antimicrobial agent may be provided in a layer 15 having a thickness "y" of between 0.1 microns and 100 microns, preferably in the range of 1.0 and 25 microns.

In another preferred embodiment, the antimicrobial agent comprising a composition of matter comprising an immobilized metal-ion sequestrant/antimicrobial comprising a metal-ion sequestrant that has a high stability constant for a target metal ion and that has attached thereto an antimicrobial metal-ion, wherein the stability constant of the metal-ion sequestrant for the antimicrobial metal-ion is less than the stability constant of the metal-ion sequestrant for the target metal-ion. These are explained in detail in U.S. patent application Ser. No. 10/868,626 filed Jun. 15, 2004 entitled AN IRON SEQUESTERING ANTIMICROBIAL COMPOSITION by Joseph F. Bringley et al.

In a preferred embodiment, the antimicrobial agent comprising a metal ion exchange material, is exchanged with at least one antimicrobial metal ion selected from silver, copper, gold, nickel, tin or zinc.

Figure 3:
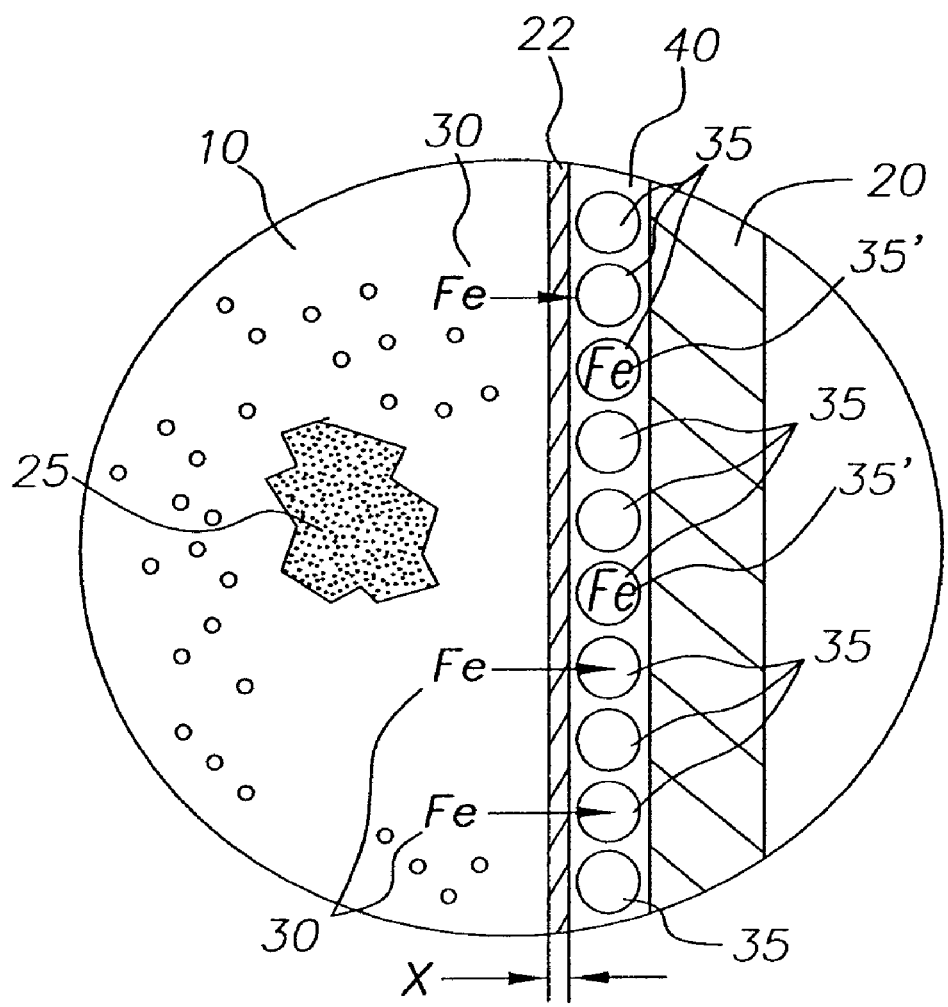
FIG. 3 is a view similar to FIG. 2 illustrating a container made in accordance with the present invention.

Referring to FIG. 3, there is illustrated an embodiment of a fluid container 5 made in accordance with the present invention. The container 5, which in the embodiment illustrated is a bottle, is made of a material that comprises a barrier layer 22, an outer polymeric layer 20 and an inner polymeric layer 40 between said barrier layer 22 and outer polymeric layer 20. The inner polymeric layer 22 contains a metal-ion sequestrant 35. The barrier layer 22 preferably does not contain the metal-ion sequestrant 35. The outer layer 20 may provide several functions including improving the physical strength and toughness of the article and resistance to scratching, marring, cracking, etc. However, the primary purpose of the barrier layer 22 is to provide a barrier through which micro-organisms 25 present in the contained fluid cannot pass. It is important to limit or eliminate, in certain applications, the direct contact of micro-organisms 25 with the metal-ion sequestrant 35 or the layer containing the metal-ion sequestrant 35, since many micro-organisms 25, under conditions of iron deficiency, may bio-synthesize molecules which are strong chelators for iron and other metals. These bio-synthetic molecules are called "siderophores" and their primary purpose is to procure iron for the micro-organisms 25. Thus, if the micro-organisms 25 are allowed to directly contact the metal-ion sequestrant 35, they may find a rich source of iron there and begin to colonize directly at these surfaces. The siderophores produced by the micro-organisms may compete with the metal-ion sequestrant for the iron (or other bio-essential metal) at their surfaces. However the energy required for the organisms to adapt their metabolism to synthesize these siderophores will impact significantly their growth rate. Thus, one object of the invention is to lower growth rate of organisms in the contained liquid. Since the barrier layer 22 of the invention does not contain the metal-ion sequestrant 35, and because micro-organisms are large, the micro-organisms may not pass or diffuse through the barrier layer 22. The barrier layer 22 thus prevents contact of the micro-organisms with the polymeric layer 40 containing the metal-ion sequestrant 35 of the invention. It is preferred that the barrier layer 22 is permeable to water. It is preferred that the barrier layer 22 has a thickness "x" in the range of 0.1 microns to 10.0 microns. It is preferred that microbes are unable to penetrate, to diffuse or pass through the barrier layer 22. Sequestrant 35 with a sequestered metal ion is indicated by numeral 35'.

Still referring again to FIG. 3, the enlarged sectioned view of the fluid container 5 illustrates a bottler having barrier layer 22, which is in direct contact with the liquid nutrient 10, an inner polymeric layer 40 and an outer polymeric layer 20. However, the bottle of FIG. 2 comprises an inner polymeric layer 15 that does not contain any metal-ion sequestering agents. In the prior art bottle illustrated in FIG. 2, the micro-organisms 25 are free to gather the "free" iron ions 30. In the example shown in FIG. 3, the inner polymer 40 contains an immobilized metal-ion sequestering agent 35 such as EDTA. In order for the metal-ion sequestering agent 35 to work properly, the inner polymer 40 containing the metal-ion sequestering agent 35 must be permeable to aqueous media. Preferred polymers for layers 22 and 40 of the invention are polyvinyl alcohol, cellophane, water-based polyurethanes, polyester, nylon, high nitrile resins, polyethylene-polyvinyl alcohol copolymer, polystyrene, ethyl cellulose, cellulose acetate, cellulose nitrate, aqueous latexes, polyacrylic acid, polystyrene sulfonate, polyamide, polymethacrylate, polyethylene terephthalate, polystyrene, polyethylene, polypropylene or polyacrylonitrile. A water permeable polymer permits water to move freely through the polymer 40 allowing the "free" iron ion 30 to reach and be captured by the agent 35. An additional barrier 22 may be used to prevent the micro-organism 25 from reaching the inner polymer material 40 containing the metal-ion sequestering agent 35. Like the inner polymer material 40, the barrier layer 22 must be made of a water permeable polymer as previously described. The micro-organism 25 is too large to pass through the barrier 22 or the polymer 40 so it cannot reach the sequestered iron ion 30 now held by the metal-ion sequestering agent 35. By using the metal-ion sequestering agents 35 to significantly reduce the amount of "free" iron ions 30 in the liquid nutrient 10, the growth of the micro-organism 25 is eliminated or severely reduced.

Figure 4:
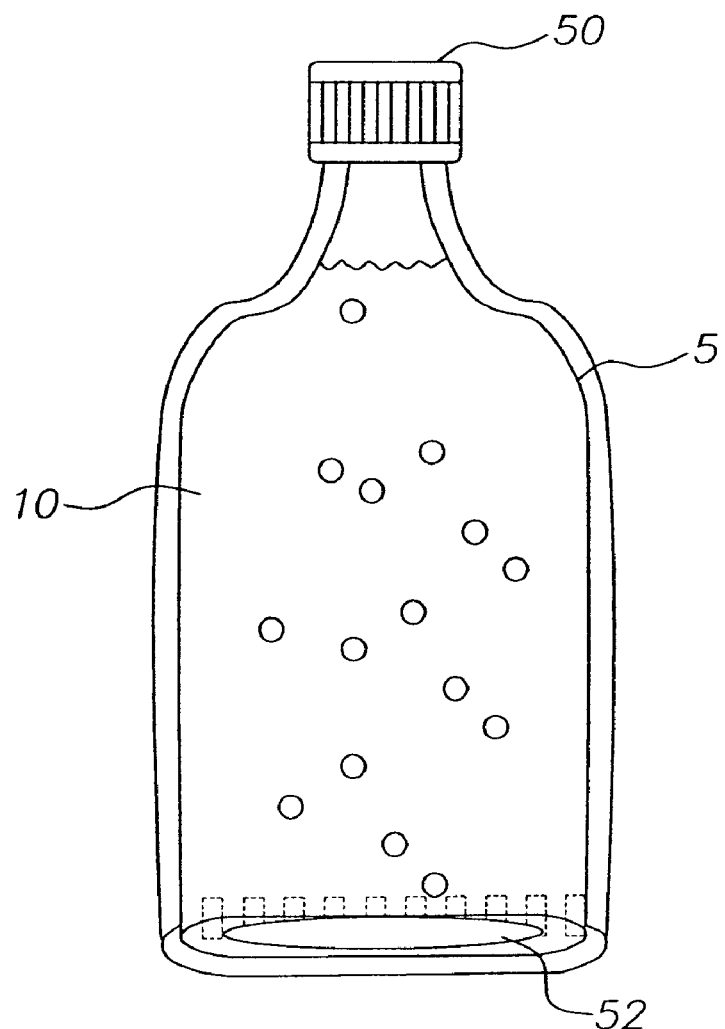
FIG. 4 illustrates a bottle with a bottle cap also made in accordance with the present invention.
Figure 5:
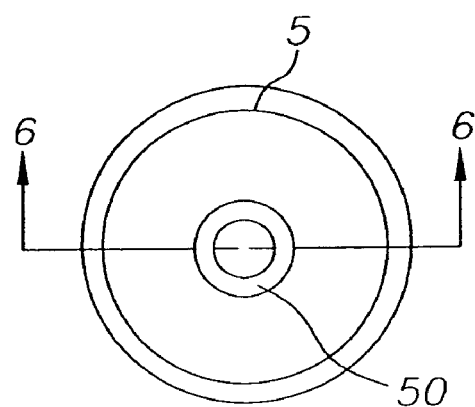
FIG. 5 is a schematic top plan view of the bottle and cap of FIG. 4.
Figure 6:
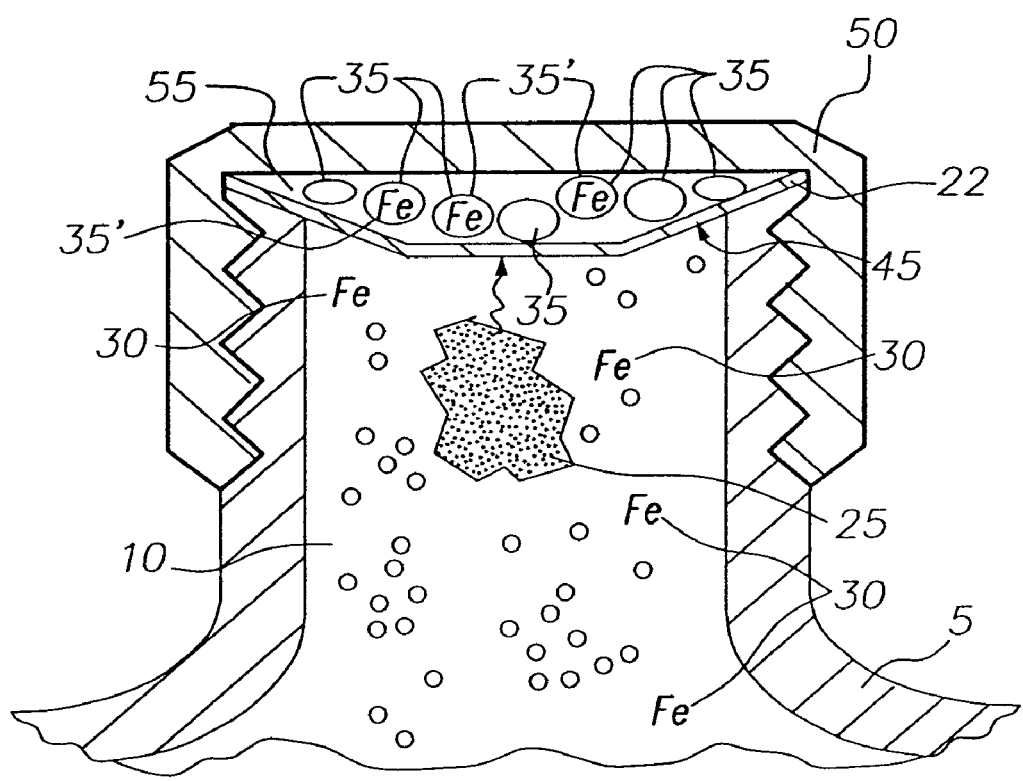
FIG. 6 is an enlarged partial cross sectional view of the bottle and cap taken along line 6-6 of FIG. 5.

In the embodiment shown in FIGS. 4, 5, and 6, the metal-ion sequestering agent 35 is contained in the bottle cap 50 instead of on the inside surface of the bottle 5. An inner portion 45 of the cap 50, which is in intimate contact with the liquid nutrient 10, is made of a hydrophilic polymer 55 containing the metal-ion sequestering agent 35 such as EDTA as described above. In some situations, the bottle may need to be placed in the inverted position in order for the sequestrant to become in contact with the contained nutrient. The cap 50 may also have the barrier layer 22 to further prevent the micro-organisms 25 from reaching the sequestered "free" iron 30. In another embodiment (not shown) the cap sealing material could be an open cell foamed structure whose cell walls are coated with the sequestering material.

In still another embodiment, the sequestering agent 35 may be in a hydrophilic polymeric insert 52 that is placed in the bottle 5 as illustrated in FIG. 4. The insert 52 may be instead of or in addition to the sequestrant in the cap 50 or interior of the bottle. The insert 52 is placed in the bottle 5 but unfolds making it too large to exit the bottle 5. In another version, the insert 52 is molded into the bottom of the bottle 5.

Figure 7:
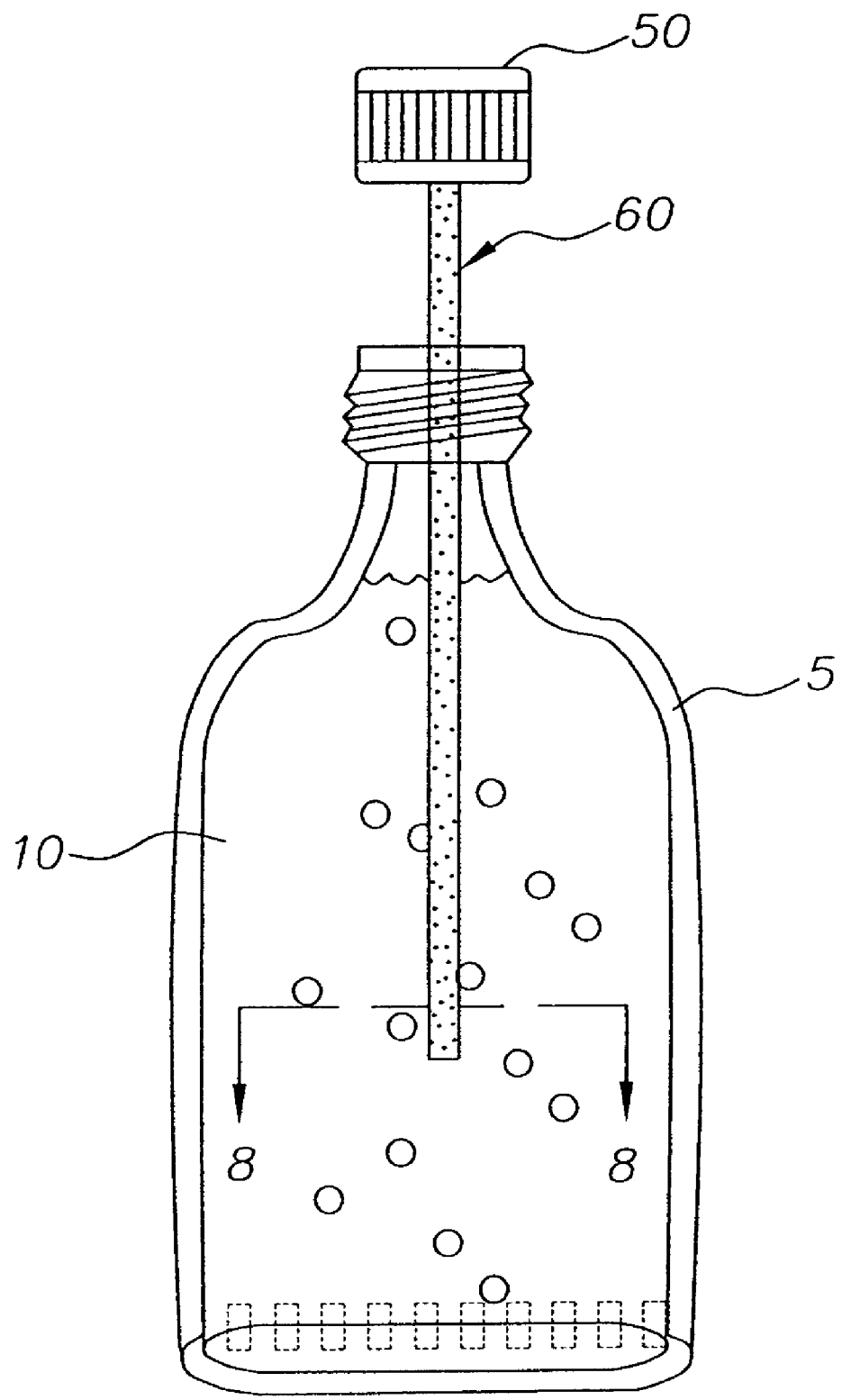
FIG. 7 is a schematic view of a projecting member extending from a modified cap of FIG. 5 also made in accordance with the present invention.
Figure 8:
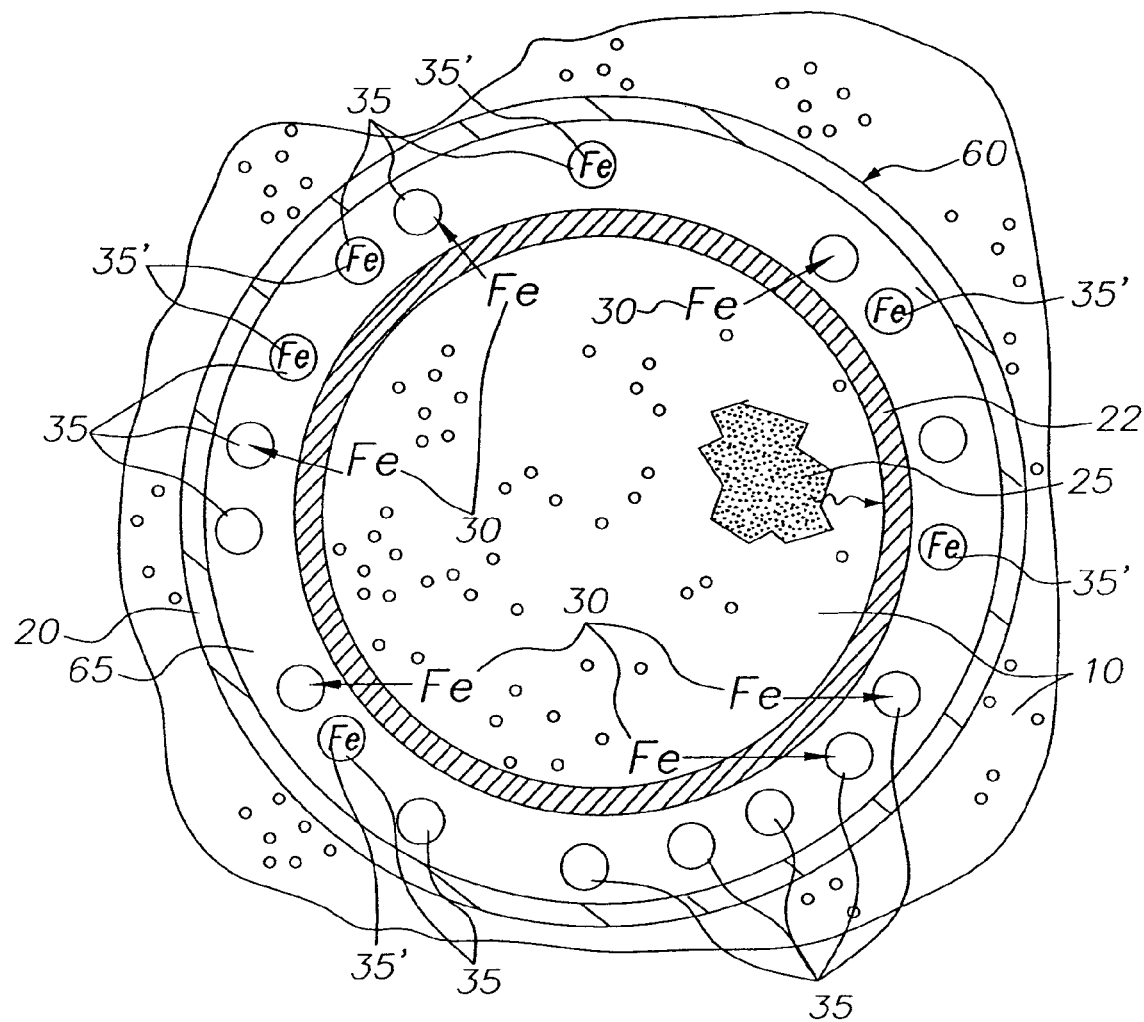
FIG. 8 is an enlarged cross sectional view of the projecting member of FIG. 7 as taken along line 8-8.

Referring to FIGS. 7 and 8, there is illustrated another modified embodiment of a container made in accordance with the present invention, like parts indicating like parts and operation as previously described. In this embodiment the metal-ion sequestering agent 35 is contained in a projecting member 60 that extends from cap 50 into the bottle 5 so that it will be in intimate contact with the liquid nutrient 10. In the embodiment, the projecting member is in the configuration of a straw that can later be used to drink the liquid content in the bottle. Like the hydrophilic polymer material lining of the inside of the bottle 5 and bottle cap 50, the extension 60 or straw is made of a hydrophilic polymer 65 containing the metal-ion sequestering agents 35 such as EDTA as described in FIG. 3. When the bottle 5 is filled with the liquid nutrient 10 such as an isotonic, and is capped, the straw 60 protrudes from the cap 50 into the solution 10 allowing the "free" iron ions 35 to be sequestered from the liquid nutrient 10. The straw 60 may also have the barrier layer 22 to further prevent the micro-organisms 25 from reaching the sequestered "free" iron ions 30. The outer layer 20 may also be made of a material similar to barrier layer 22 so that "free" iron ions 30 can reach the sequestrant 35 from the outside of the straw 60.

In the example shown the extension is a straw but the extension can be of any shape just as long as it extends into the food or beverage establishing intimate contact.

Figure 9:
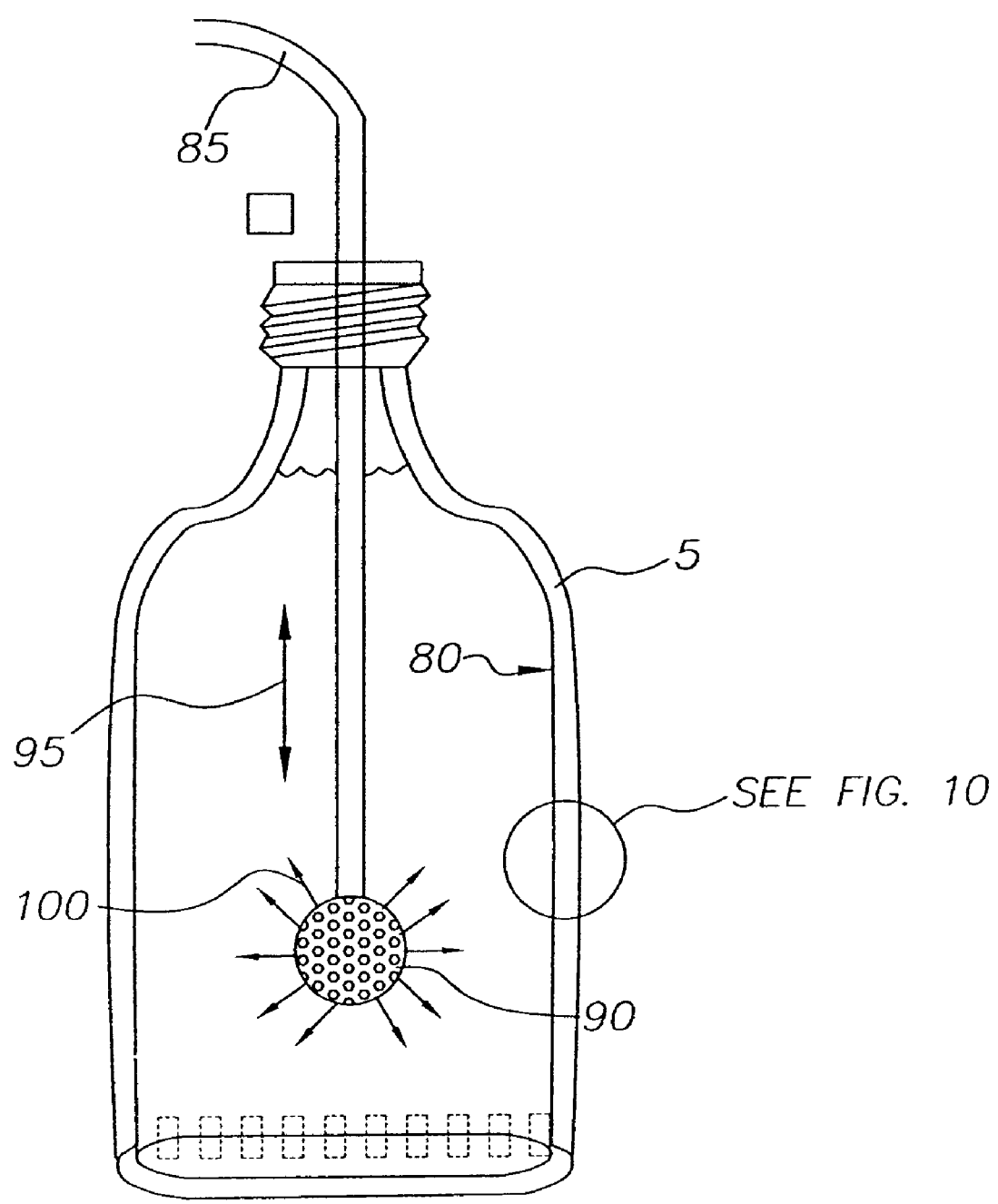
FIG. 9 is a schematic view of another embodiment of the present invention illustrating one method for applying a coating to the interior surface of a bottle made in accordance with the present invention.
Figure 10:
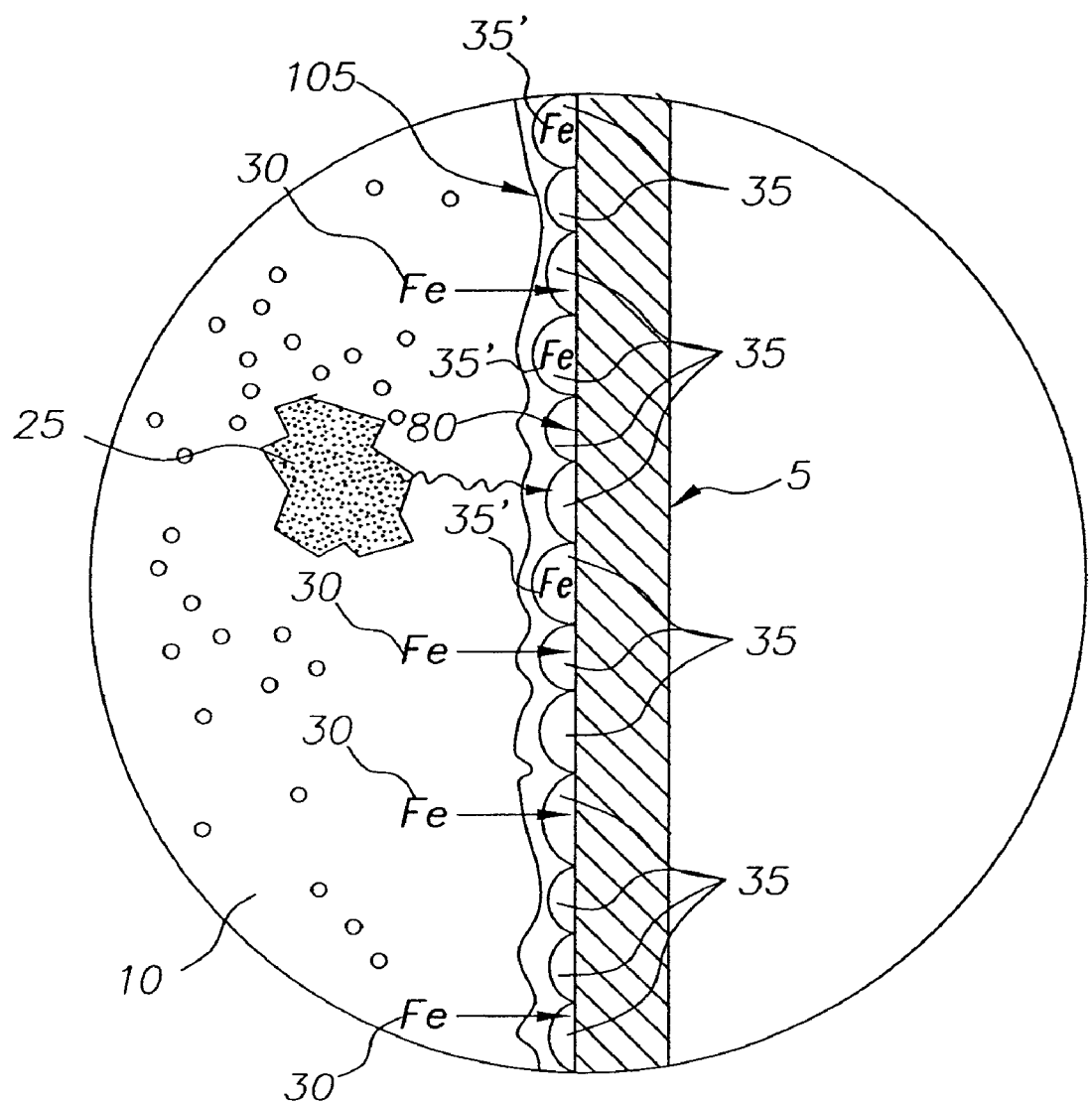
FIG. 10 is an enlarged partial cross sectional view of a portion of the bottle of FIG. 9 illustrating the sprayed coating of the ion sequestering agent.

Referring to FIGS. 9 and 10, there is illustrated another embodiment of a bottle 5 made in accordance with the present invention. In this embodiment, the metal-ion sequestering agent 35 is applied to the inside surface 80 of the bottle 5 by spraying a metal-ion sequestering agent 35, for example EDTA, on to the inside surface of the bottle through a supply tube 85 using a spherical shaped nozzle assembly 90. The nozzle assembly 90 is moved up and down in the direction of the arrow 95 while the metal-ion sequestering agent 35 is sprayed as indicated by the arrows 100. The method of applying coatings to glass, metal or plastic containers is well known to those skilled in the art. FIG. 10 illustrates an enlarged partial cross sectional view of the portion of the bottle of FIG. 9 where the spray coating 105 of the ion sequestering agent 35 has been applied. As previously discussed in FIG. 3, like numerals indicate like parts and operations. It is of course understood that the inner layer containing the sequestrant may be applied or formed on the inside surface of the container in any appropriate manner. The bottle 5 in this embodiment may be made of any appropriate plastic or glass material.

Figure 11:
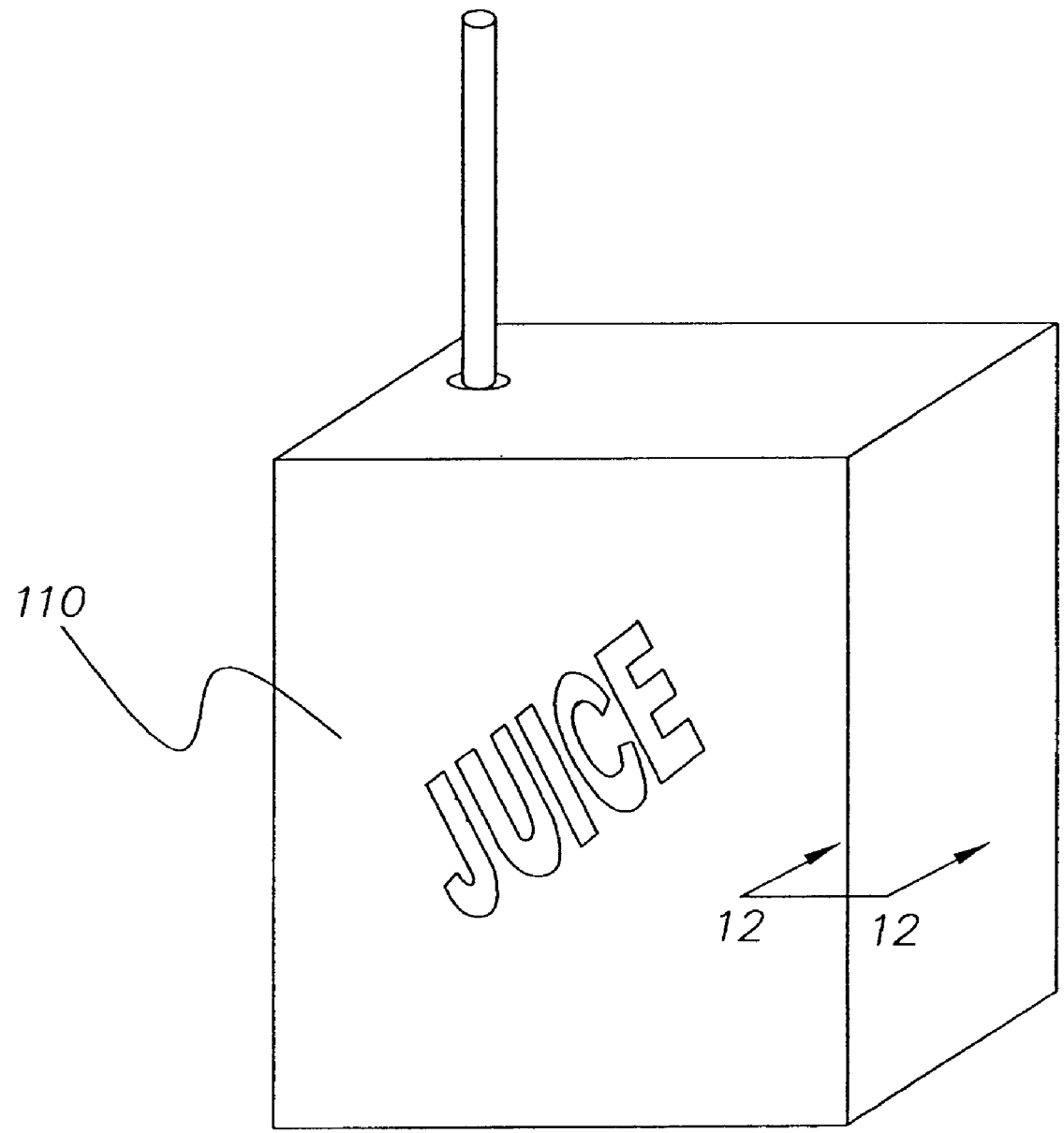
FIG. 11 is a schematic view of another fluid container made accordance with the present invention such as a juice box.
Figure 12:
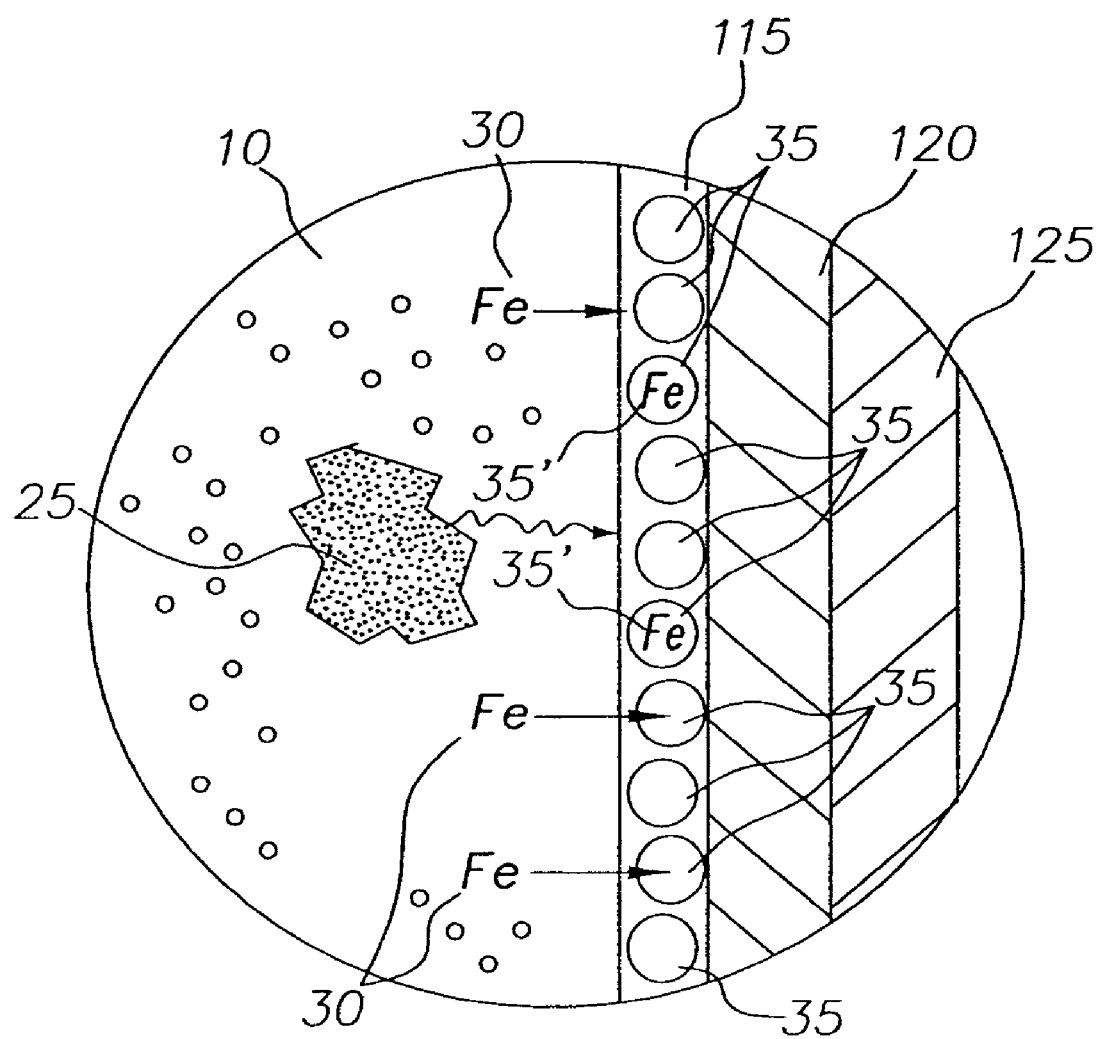
FIG. 12 is an enlarged partial cross sectional view of the juice box taken along line 12-12 of FIG. 11.

Referring to FIGS. 11 and 12, there is illustrated yet another modified container 110 made in accordance with the present invention. In particular the container comprises juice/drink box 110 for containing a liquid beverage. The box 110 is made of a sheet material that comprises inner layer 115, a middle layer 120 made of a hydrophobic polymer material, and an outer layer 125. The inner layer 115 is in direct contact with the liquid nutrient 10 and is made of a hydrophilic polymer containing the metal-ion sequestering agent 35 such as EDTA as described above in FIG. 3. As previously discussed in FIG. 3, like numerals indicate like parts and operations. The outer layer 125 may comprise a foil wrap.

Figure 13:
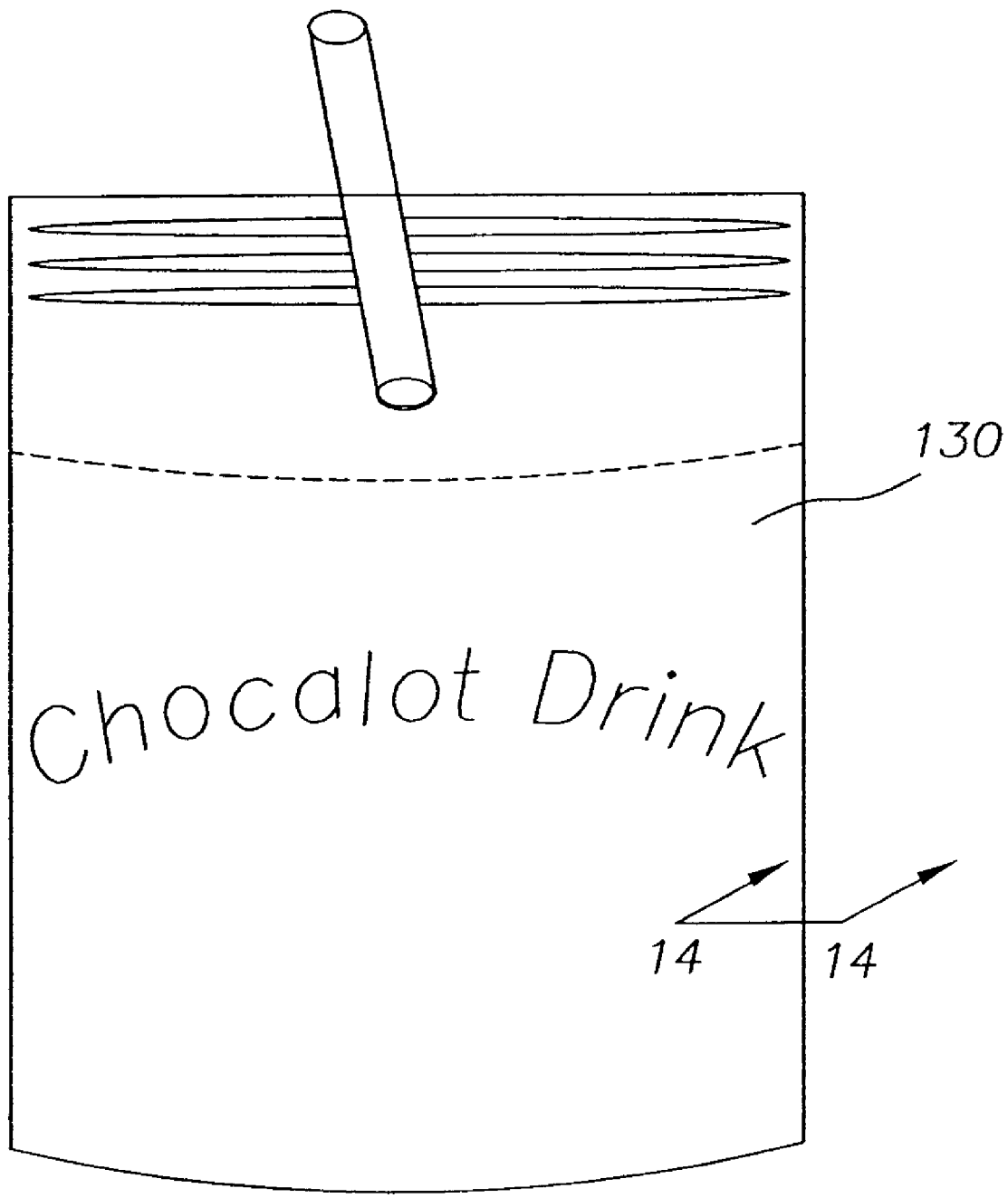
FIG. 13 is a schematic view of yet another fluid container such as a stand up pouch made in accordance with the present invention.
Figure 14:
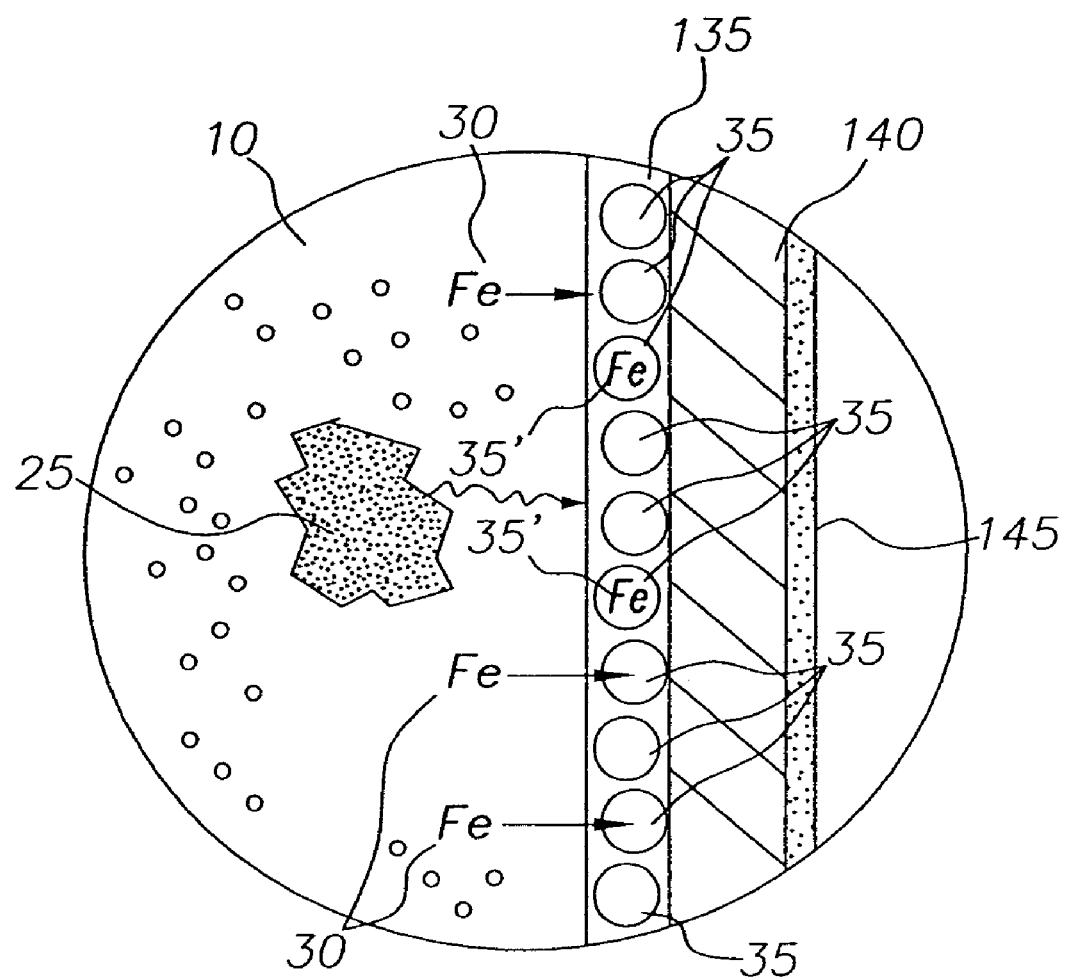
FIG. 14 is an enlarged partial cross sectional view of the stand up pouch taken along line 14-14 of FIG. 13.

Referring to FIGS. 13 and 14, there is illustrated yet another modified embodiment of a container 130 made in accordance with the present invention. In the embodiment, the container comprises a stand up pouch 130. The pouch 130 comprises an inner layer 135 made of a hydrophilic polymer material, and an outer layer 140. The outer layer 140 may be made of a polymer such as Mylar™ with a metalized coating 145. The inner layer 135 is in direct contact with the liquid nutrient 10 and is made of a hydrophilic polymer containing the metal-ion sequestering agent 35 such as EDTA as described above in FIG. 3. The stand up pouch 130 may also have the barrier layer 22 not shown to further prevent the micro-organisms 25 from reaching the sequestered "free" iron 30. As previously discussed in FIG. 3, like numerals indicate like parts and operations.

Figure 15:
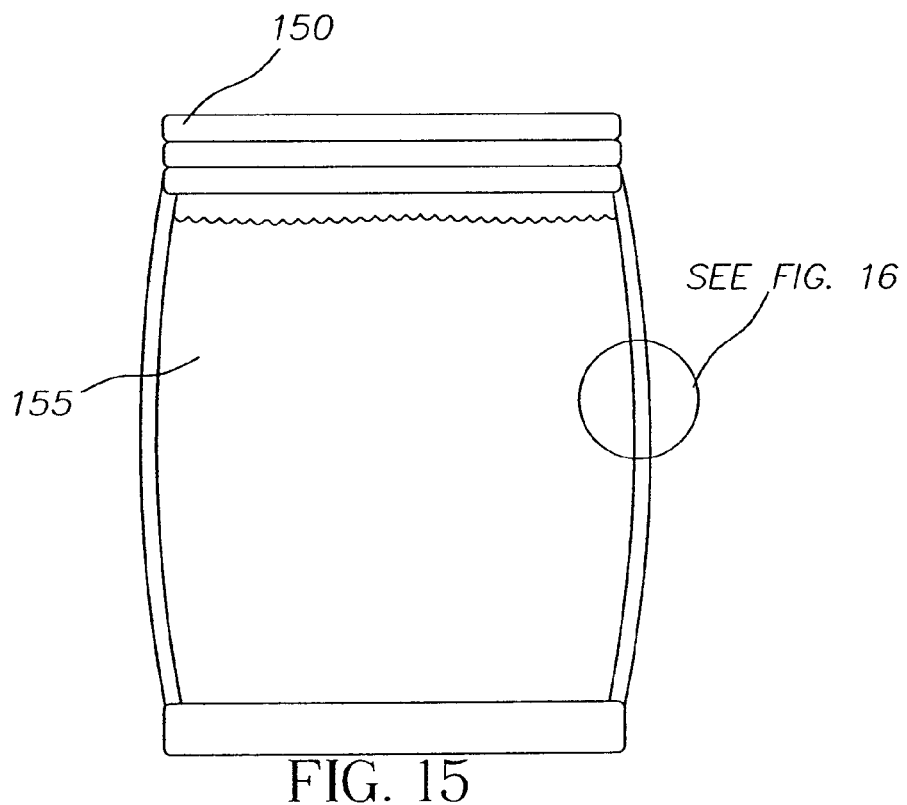
FIG. 15 is a schematic view of still another embodiment of a fluid container such as a bag also made in accordance with the present invention.
Figure 16:
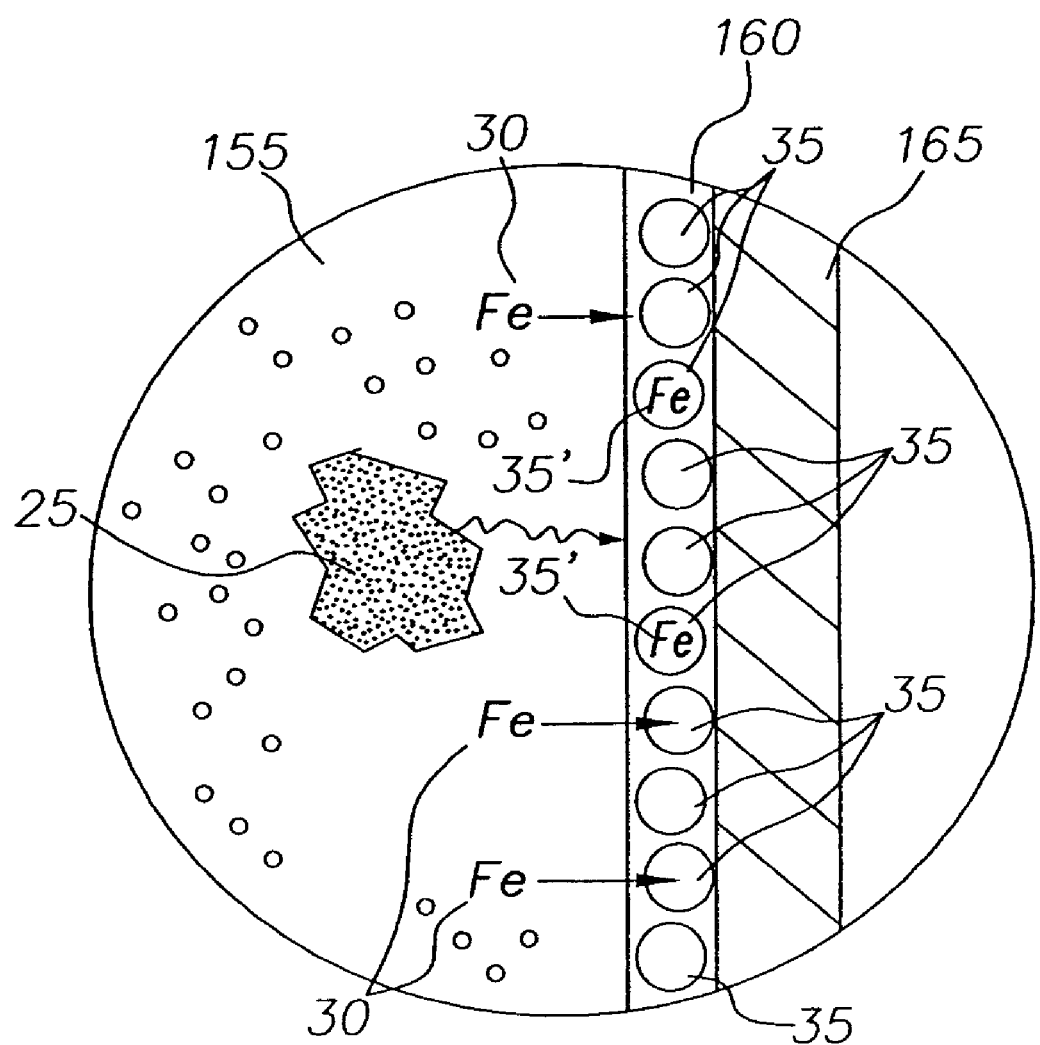
FIG. 16 is an enlarged partial cross sectional view of a portion of the bag of FIG. 15 as indicated by circle 16.

Referring to FIGS. 15 and 16, there is illustrated still another modified container made in accordance with the present invention. In this embodiment the container comprises a bag 150. The bag 150, which is intended to hold an aqueous material, comprises an inner layer 155 made of a hydrophobic polymer material and an outer layer 160. The outer layer 140 may be made of a polymer such as polyethylene terephthalate. The inner layer 155 is in direct contact with the aqueous material 155 and is made of a hydrophilic polymer containing the metal-ion sequestering agent 35 such as EDTA as described above in FIG. 3. The bag 150 may also have the barrier layer 22 not shown to further prevent the micro-organisms 25 from reaching the sequestered "free" iron 30. As previously discussed in FIG. 3, like numerals indicate like parts and operations.

Figure 17:
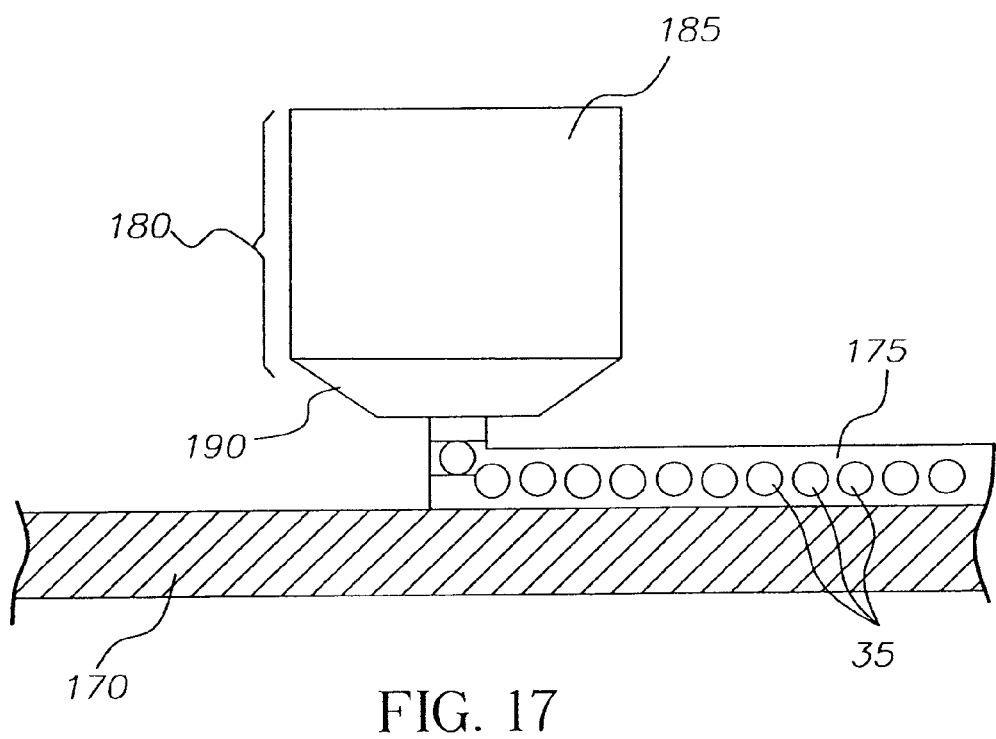
FIG. 17 is a cross-sectional view of a web that can be used in the manufacture of a box, pouch or bag showing a coating assembly for coating a hydrophilic layer containing a metal-ion sequestering agent.

The juice box 110, the pouch 130 and the bag 150 may be constructed from a base web 170 as illustrated in FIG. 17. After the base web 170 is formed, the hydrophilic layer 175 is applied via a coating assembly 180 comprised of a reservoir 185, an applicator 190 and a drive mechanism (not shown) to form the hydrophilic inner layer 175 containing the metal-ion sequestering agent 35 as described above in FIG. 3. Other methods of forming and of making webs and applying a coating such as coextrusion maybe used. It is of course understood that any suitable technique or process may be used for applying a coating on supporting web as long as the coating has the appropriate sequestrant.

Figure 18:
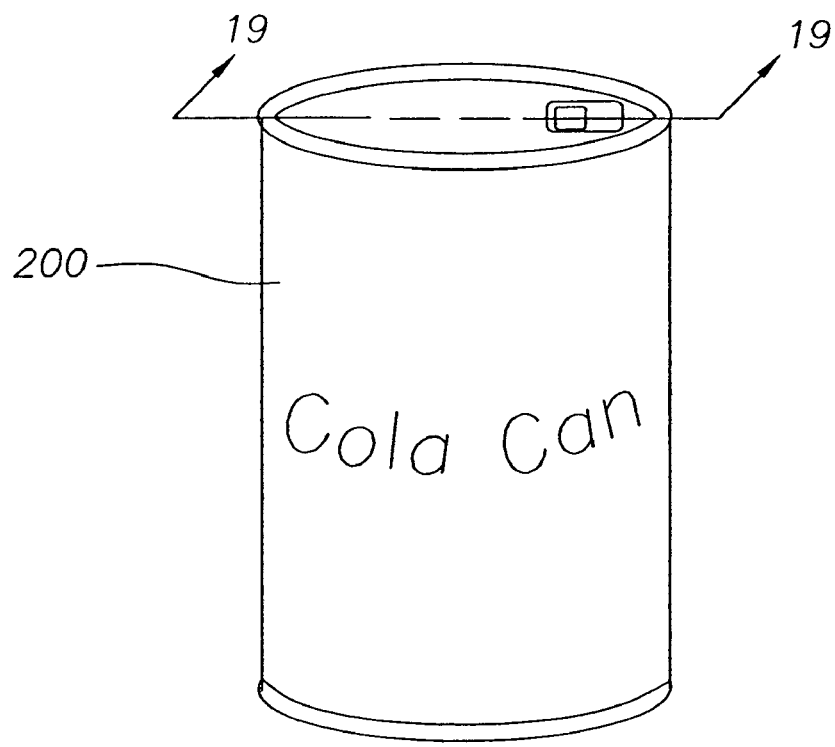
FIG. 18 is a schematic view of yet another fluid container, such as a can, made in accordance with the present invention.
Figure 19:
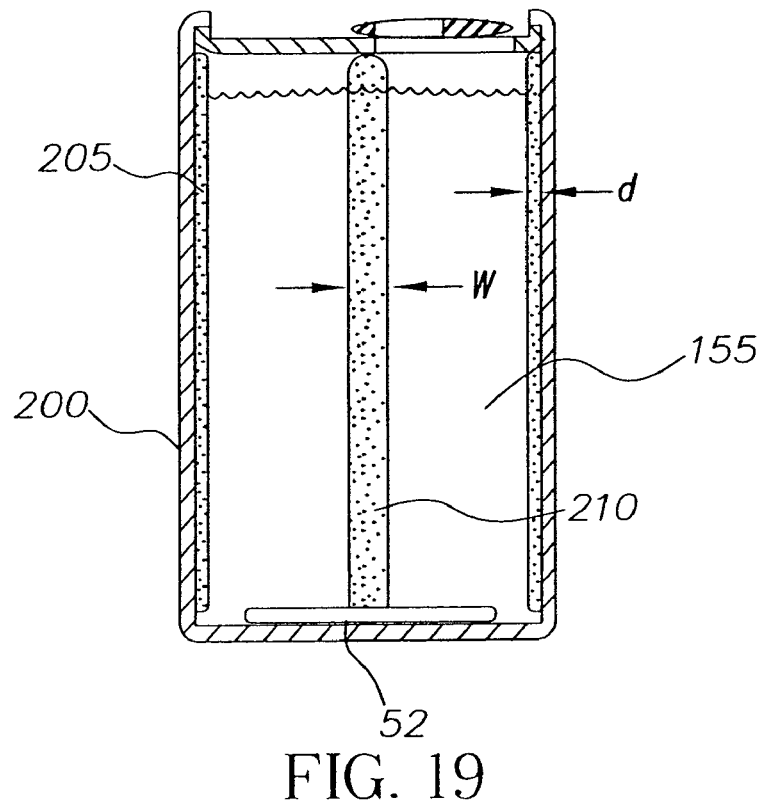
FIG. 19 is a cross sectional view of FIG. 18 as taken along line 19-19.

Referring to FIGS. 18 and 19 there is illustrated and modified container 220 made in accordance with the present invention. In this embodiment, the container 220 comprises a can. The can 200 is made of a metal material such as aluminum or steel, and has a top and a bottom, which may or may not be made as separate piece. The can 200 may also have a lining 205, which is in direct contact with the aqueous material 155 and intended to prevent corrosion of the metal by the contents of the can. The construction of metal cans is well known by one skilled in the art. The lining 205 may include a hydrophilic polymer containing the metal-ion sequestering agent 35 or have a hydrophilic polymer strip 210 containing metal-ion sequestering agent 35 made as part of lining 205 of the can 200. The strip 210 may have a width "w" of between 1 millimeter and 30 millimeters and be spaced at intervals around the inside circumference of the can 200 and a depth "d" of −1.0 to 10 micrometers. In still another embodiment, the sequestering agent 35 may be in a hydrophilic polymeric insert 52. The insert 52 is placed in the can 200 but unfolds making it too large to exit the can 200. The insert 52 may be simply placed on the bottom of the container or if desired secured to the interior surface of the container in some fashion. The metal-ion sequestering agent performs as previously described above in FIG. 3.

Figure 20:
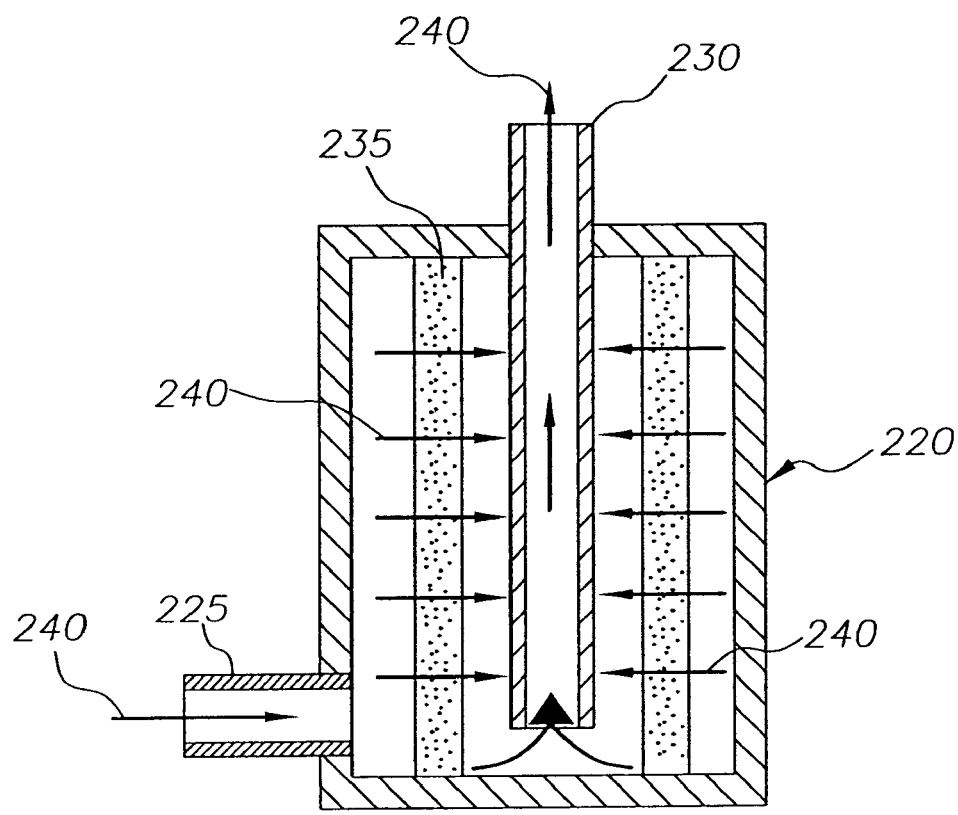
FIG. 20 is a cross sectional view of a filter assembly made in accordance with the present invention.

Referring to FIG. 20, there is illustrated a cross-sectional view of a filter assembly 220 comprising an inlet port 225, an outlet port 230, and a filter 235. The filter 235 contains an immobilized metal-ion sequestering agent as previously described. As the solution flows through the filter assembly 220 in the direction indicated by the arrows 240 and through the filter 235 the metal ions in the solution are sequestered and removed by the metal-ion sequestering agent 245.

Figure 21:
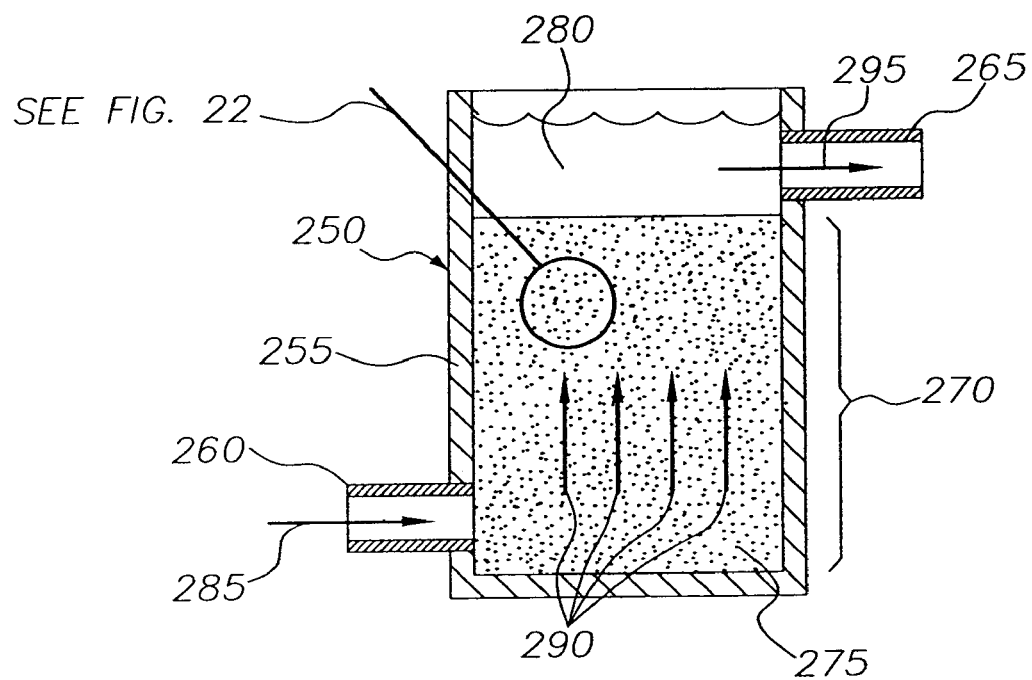
FIG. 21 is a cross sectional view of a fluid bed ion exchange assembly made in accordance with the present invention.

Referring to FIG. 21, there is illustrated a cross sectional view of a fluid bed ion exchange assembly 250 comprising a holding tank 255, an inlet port 260, an outlet port 265, and a fluid bed 270 containing a metal-ion sequestering material 275 made in accordance with the present invention. The solution 280 flows into the fluid bed ion exchange assembly 250 via inlet port 260 as indicated by arrow 285 through the metal-ion sequestering material 275 in fluid bed 270 as indicated by arrows 290 and out the outlet port as indicated by arrow 295.

Figure 22:
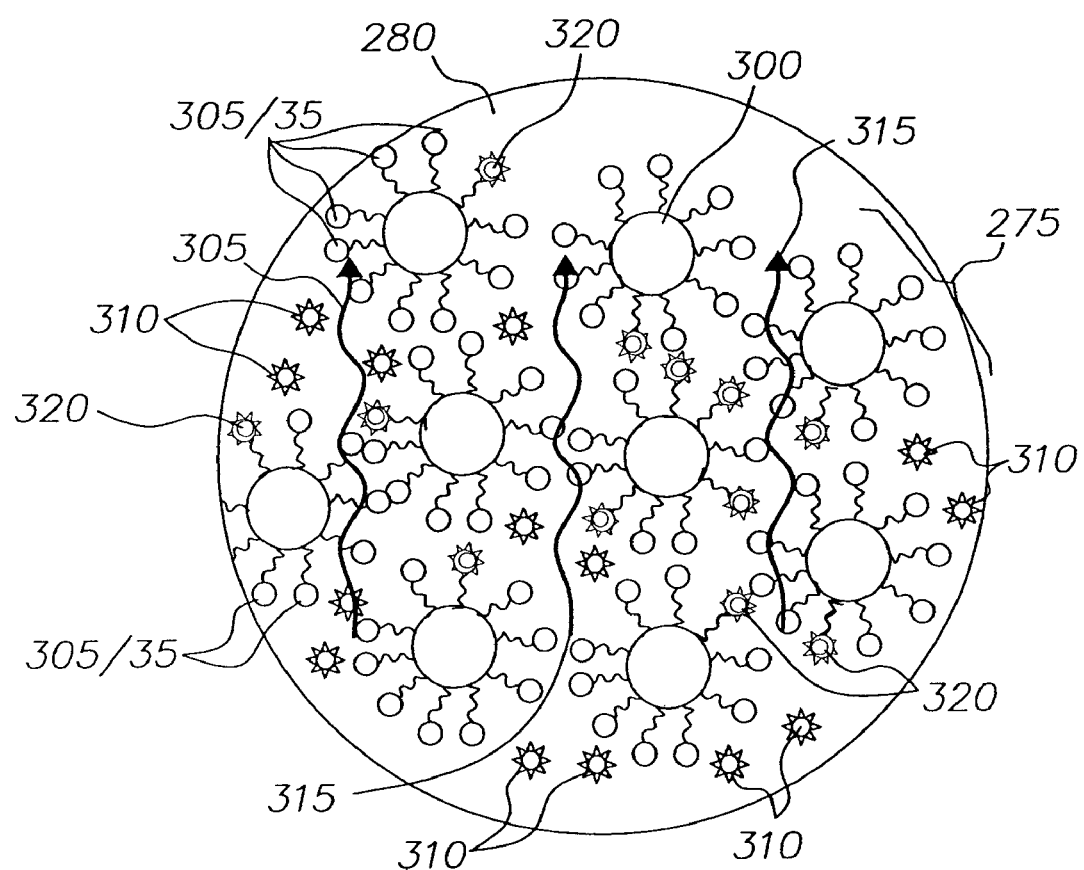
FIG. 22 is an enlarged partial view of a portion of the fluid bed ion exchange assembly of FIG. 21 as identified by circle 22 illustrating a metal-ion sequestering agent.

FIG. 22 is an enlarged partial view of a portion of the fluid bed 270 containing a metal-ion sequestering material 275. An example of the metal-ion sequestering material 275 comprises a core material 300 and a shell material 305 made of the metal-ion sequestering agent 35 as described in U.S. patent application Ser. No. 10/822,940 filed Apr. 13, 2004 entitled DERIVATIZED NANOPARTICLE COMPRISING METAL-ION SEQUESTRANT by Joseph F. Bringley et al. As previously described above in FIG. 21, the solution 280 containing "free" metal ions 310 flows through the fluid bed 270 as indicated by the arrows 315. As the solution 280 flows through the fluid bed 270 the shell material 305 made of the metal-ion sequestering agent 35 gathers the metal ions 320 removing them from the solution, which then flow out through the outlet port 265.

While in the embodiments discussed, the iron sequestering agent or antimicrobial agent may be provided only on a portion of the contacting surface of the bottle or other container. For example, but not limited to, the agents may be provided only on the body portion of a bottle and not the neck portion.

While in many of the embodiments illustrated a barrier layer is not discussed, it is to be understood that a barrier layer 22 may be provided in any of the embodiments for preventing the microbes (micro-organism) from contacting the sequestrant.

Figure 23:
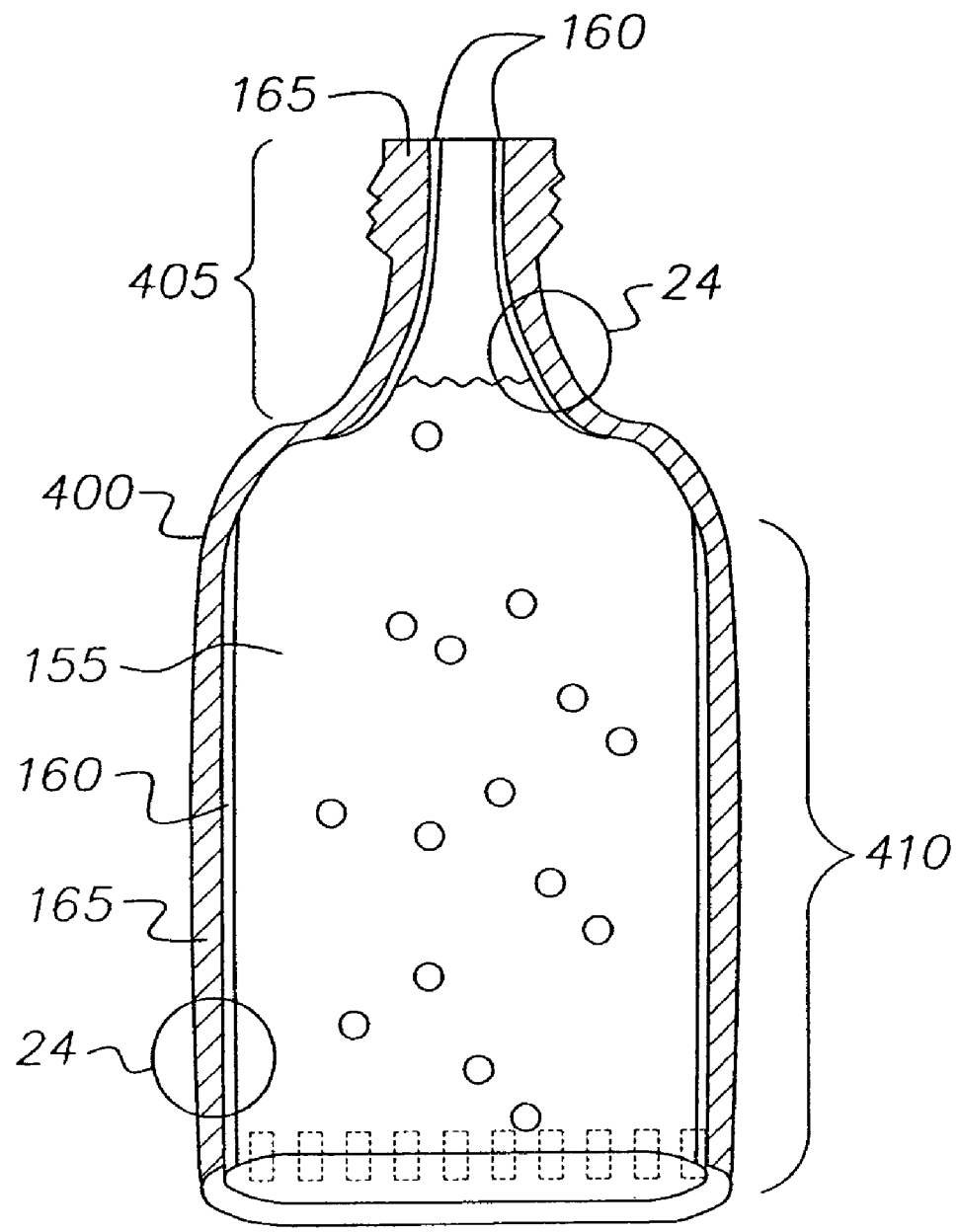
FIG. 23 illustrates another embodiment of a cross section of a fluid container made in accordance with the prior art.
Figure 24:
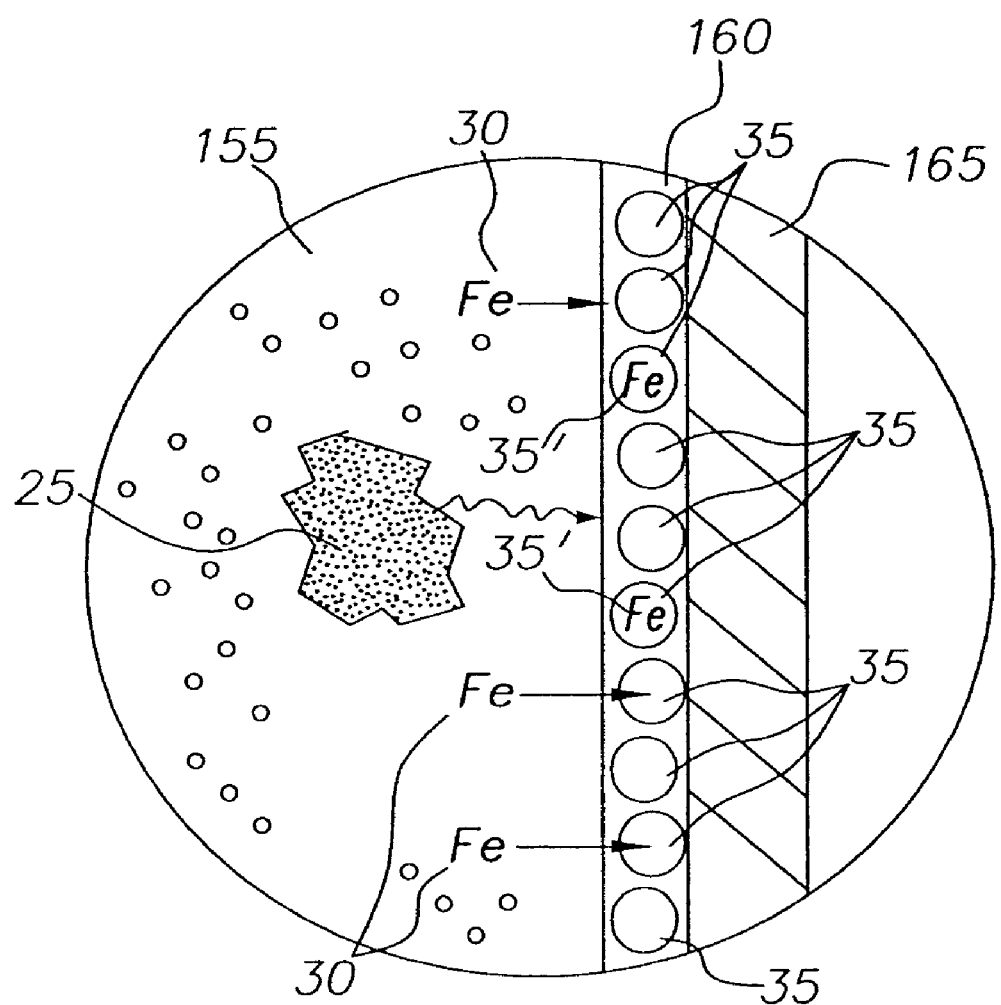
FIG. 24 is an enlarged partial cross sectional view of both the neck portion and body portion of the container of FIG. 23 illustrating a "free" iron ion-sequestering agent.

Referring now to FIGS. 23 and 24, there is illustrated a cross sectional view of another embodiment of the container 400 made in accordance with the art of the present invention. In the embodiment shown the metal-ion sequestering agent is provided in a localized area of the interior of the container 400. In the embodiment illustrated an inner layer 160 is formed only in the neck portion/area 405 or alternatively may be formed only in the body portion 410 of the container 400 using one of the following molding methods; the two shot molding, insert mold or two shot injection stretch blow molding. All three methods are known to those skilled in the art. While inner layer 160 is described as being only in one of these two locations, the inner layer 160 may be provided in both locations or any other desired location.

Referring to FIG. 24, there is illustrated an enlarged partial cross sectional view of the neck portion 405 and of the body portion 410 of the container 400 of FIG. 23. The neck portion 405 of the container 400 is intended to hold an aqueous material 155, wherein the inner layer 160 made of a hydrophobic polymer material and an outer layer 165. The outer layer 165 may be made of a polymer such as poly-ethylene terephthalate. The inner layer 160 is in direct contact with the aqueous material 155 and is made of a hydrophilic polymer containing the metal-ion sequestering agent 35 such as EDTA as described above in FIG. 3. As previously discussed in FIG. 3, like numerals indicate like parts and operations. Similarly the body portion 410 of the container 400 may be produced in the same manner as described above.

EXAMPLES AND COMPARISON EXAMPLES

Materials:

Colloidal dispersions of silica particles were obtained from ONDEO Nalco Chemical Company. NALCO® 1130 had a median particle size of 8 nm, a pH of 10.0, a specific gravity of 1.21 g/ml, a surface area of about 375 $m^2/g$, and a solids content of 30 weight percent. N-(trimethoxysilylpropyl ethylenediamine triacetic acid, trisodium salt was purchased from Gelest Inc., 45% by weight in water.

Preparation of Derivatized Nanoparticles. To 600.00 g of silica NALCO® 1130 (30% solids) was added 400.00 g of distilled water and the contents mixed thoroughly using a mechanical mixer. To this suspension, was added 49.4 g of N-(trimethoxysilyl) propylethylenediamine triacetic acid, trisodium salt in 49.4 g distilled water with constant stirring at a rate of 5.00 ml/min. At the end of the addition the pH was adjusted to 7.1 with the slow addition of 13.8 g of concentrated nitric acid, and the contents stirred for an hour at room temperature. Particle size analysis indicated an average particle size of 15 nm. The percent solids of the final dispersion was 18.0%.

Preparation of the Immobilized Metal-ion Sequestrant/Antimicrobial: 200.0 g of the above derivatized nanoparticles were washed with distilled water via dialysis using a 6,000-8,000 molecular weight cutoff filter. The final ionic strength of the solution was less than 0.1 millisemens. To the washed suspension was then added with stirring 4.54 ml of 1.5 M $AgNO_3$ solution, to form the immobilized metal-ion sequestrant/antimicrobial.

Preparation of Polymeric Layers of Immobilized Metal-ion Sequestrants and Sequestrant/Antimicrobials.

Coating 1 (comparison). A coating solution was prepared as follows: 8.8 g of a 40% solution of the polyurethane Permax 220 (Noveon Chemicals) was combined with to 90.2 grams of pure distilled water and 1.0 g of a 10% solution of the surfactant OLIN 10G was added as a coating aid. The mixture was then stirred and blade-coated onto a polymeric support using a 150 micron doctor blade. The coating was then dried at 40-50° C., to produce a film having 5.4 $g/m^2$ of polyurethane.

Coating 2. A coating solution was prepared as follows: 171.2 grams of the derivatized nanoparticles prepared as described above were combined with 64.8 grams of pure distilled water and 62.5 g of a 40% solution of the polyurethane Permax 220 (Noveon Chemicals). 1.5 g of a 10% solution of the surfactant OLIN 10G was added as a coating aid. The mixture was then stirred and blade-coated onto a polymeric support using a 150 micron doctor blade. The coating was then dried at 40-50° C., to produce a film having 5.4 $g/m^2$ of the derivatized nanoparticles and 5.4 $g/m^2$ of polyurethane.

Coating 3. A coating solution was prepared as follows: 171.2 grams of the derivatized nanoparticles prepared as described above were combined with 33.5 grams of pure distilled water and 93.8 g of a 40% solution of the polyurethane Permax 220 (Noveon Chemicals). 1.5 g of a 10% solution of the surfactant OLIN 10G was added as a coating aid. The mixture was then stirred and blade-coated onto a polymeric support using a 150 micron doctor blade. The coating was then dried at 40-50° C., to produce a film having 5.4 g/m² of the derivatized nanoparticles and 8.1 g/m² of polyurethane.

Coating 4. A coating solution was prepared as follows: 138.9 grams of the derivatized nanoparticles prepared as described above were combined with 97.1 grams of pure distilled water and 62.5 g of a 40% solution of the polyurethane Permax 220 (Noveon Chemicals). 1.5 g of a 10% solution of the surfactant OLIN 10G was added as a coating aid. The mixture was then stirred and blade-coated onto a polymeric support using a 150 micron doctor blade. The coating was then dried at 40-50° C., to produce a film having 4.4 g/m² of the derivatized nanoparticles and 5.4 g/m₂ of polyurethane.

Coating 5. A coating solution was prepared as follows: 12.8 grams of the immobilized metal-ion sequestrant/antimicrobial suspension prepared as described above was combined with to 77.4 grams of pure distilled water and 8.8 g of a 40% solution of the polyurethane Permax 220 (Noveon Chemicals). 1.0 g of a 10% solution of the surfactant OLIN 10G was added as a coating aid. The mixture was then stirred and blade-coated onto a polymeric support using a 150 micron doctor blade. The coating was then dried at 40-50° C., to produce a film having 2.7 g/m² of the immobilized metal-ion sequestrant/antimicrobial, 0.06 g/m² silver-ion and 5.4 g/m² of polyurethane.

Testing Methodology

A test similar to ASTM E 2108-01 was conducted where a piece of a coating of known surface area was contacted with a solution inoculated with micro-organisms. In particular a piece of coating 1×1 cm was dipped in 2 ml of growth medium (Trypcase Soy Agar 1/10), inoculated with 2000 CFU of *Candida albicans* (ATCC-1023) per ml. Special attention was made to all reagents to avoid iron contamination with the final solution having an iron concentration of 80 ppb before contact with the coating.

Micro-organism numbers in the solution were measured daily by the standard heterotrophic plate count method.

Figure 25:
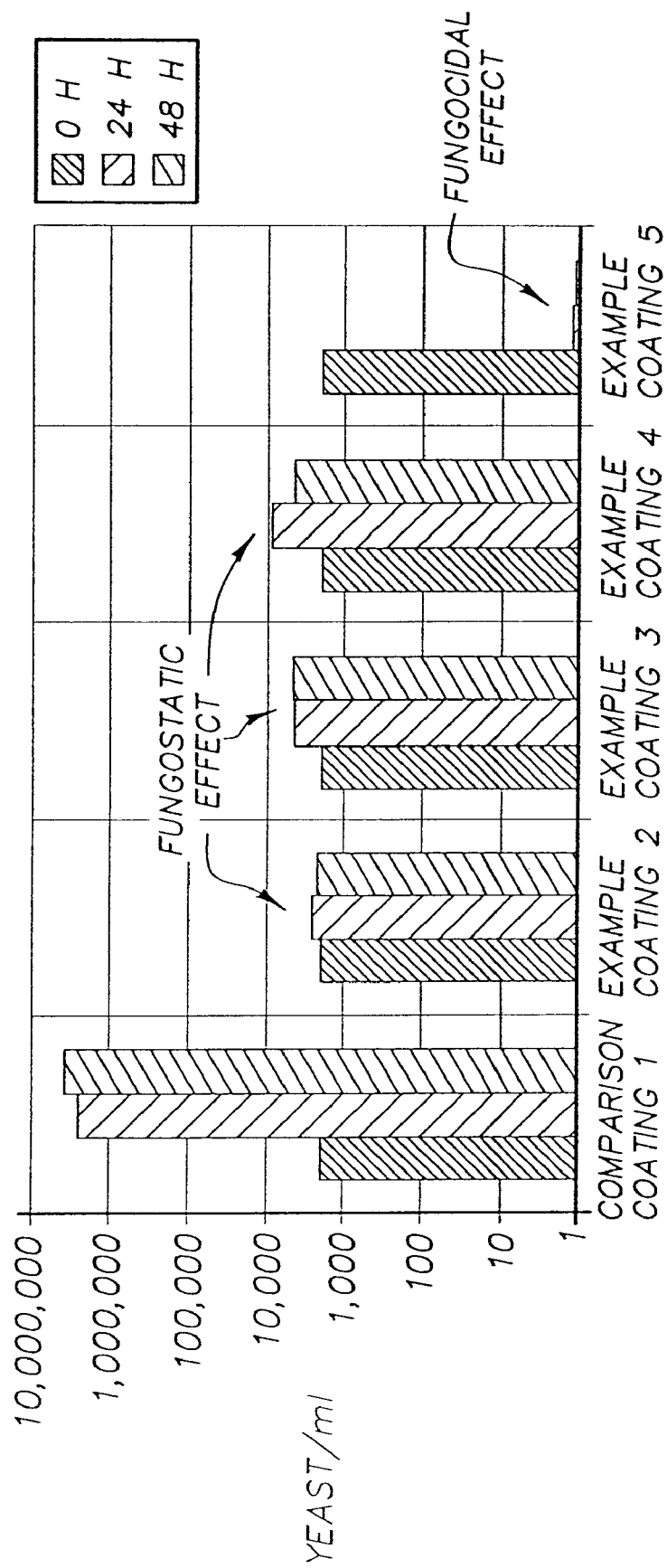
FIG. 25 is a bar graph illustrating fungostatic and fungicidal effects of the invention on example yeast populations.

The bar graph shown in FIG. 25 demonstrates the effectiveness of the inventive examples. The yeast population which was exposed to the comparison coating 1 (which contained no derivatized nanoparticles) showed a growth factor of one thousand during 48 hours (a 1000-fold increase in population). The yeast population which was exposed to the example coatings 2-4 (containing derivatized nanoparticles) showed growth factors of only 1-4. This is indicative of a fungostatic or bio-static effect in which the population of organisms is kept at a constant or near constant level, even in the presence of a medium containing adequate nutrient level. The yeast population which was exposed to the example coating 5 (derivatized nanoparticles that had been ion exchanged with silver ion—a known antimicrobial) showed a fungicidal effect (the yeast were completely eliminated). The low level of silver when coated by itself without the nanoparticles would not be expected to exhibit this complete fungicidal effect, and there appears to be a synergistic effect between the iron sequestration and the release of antimicrobial silver.

As can be seen from the bar graph illustrated in FIG. 25, significant improved results may be obtained when a metal-ion sequestering agent is used in conjunction with an antimicrobial agent. The combined agents reduced the level of microbes to lower level than when first introduced and then maintained the reduced level of microbes in the liquid nutrient.

The invention has been described in detail with particular reference to certain preferred embodiments thereof but it will be understood that variations and modifications can be effected within the spirit and scope of the invention.

Parts List 5 fluid container/bottle
10 liquid nutrient
15 inner polymeric layer
20 outer polymeric layer
22 barrier layer
25 micro-organism
30 "free" iron ion
35 metal-ion sequestering agents
35' metal-ion sequestering agent with a sequestered metal ion
40 hydrophilic polymer
45 inner portion
50 bottle cap
52 insert
55 hydrophilic polymer
60 extension (straw)
65 hydrophilic polymer
80 inside surface
85 supply tube
90 spherical shaped nozzle assembly
95 arrow
100 arrow
105 spray coating
110 juice box
115 inner layer
120 middle layer
125 outer layer
130 pouch
135 inner layer
140 outer layer
145 coating
150 bag
155 aqueous material
160 inner layer
165 outer layer
170 base web
175 hydrophilic layer
180 coating assembly
185 reservoir
190 applicator
200 can
205 lining
210 strip
220 filter assembly
225 inlet port
230 outlet port
235 filter
240 arrow
250 fluid bed ion exchange assembly
255 holding tank
260 inlet port
265 outlet port
270 fluid bed
275 sequestering material
280 solution 285 arrow
290 arrow
295 arrow
300 core material
305 shell material
310 "free" metal ions
315 arrows
320 gathered metal ions
400 container
405 neck portion
410 body portion

What is claimed is:

1. A fluid container for containing a liquid nutrient having a pH equal to or greater than about 2.5, said container having an interior surface having a metal-ion sequestering agent provided in a localized area of the interior surface and immobilized on the interior surface, said sequestering agent having a high selectivity for certain metal ions and a low-affinity for at least one other ion, the container formed by a two shot molding, insert molding or two shot injection stretch blow molding process, said metal ion sequestering agent provided for removing a designated metal ion from said liquid nutrient for inhibiting growth of microbes in said liquid nutrient and an antimicrobial agent provided for at least maintaining an amount of microbes in said liquid nutrient to a prescribed condition, wherein said metal-ion sequestering a agent comprises derivatized nanoparticles comprising inorganic nanoparticles having an attached metal-ion sequestrant, wherein said inorganic nanoparticles have an average particle size of less than 200 nm and the derivatized nanoparticles have a stability constant greater than $10^{10}$ with iron (III), and wherein said metal ion sequestrant is attached to the nanoparticles by reacting the nanoparticles with a silicon alkoxide intermediate of the sequestrant having the general formula:

$Si(OR)_{4-x}R'_x$;

wherein x is an integer from 1 to 3;

R is an alkyl group; and

R' is an organic group containing an alpha amino carboxylate, a hydroxamate, or a catechol.

2. The fluid container of claim 1 wherein said metal-ion sequestering agent has a stability constant greater than $10^{20}$ with iron (III).

3. The fluid container of claim 1 wherein said antimicrobial agent comprises an antimicrobial active material selected from benzoic acid, sorbic acid, nisin, thymol, allicin, peroxides, imazalil, triclosan, benomyl, metal-ion release agents, metal colloids, anhydrides, and organic quaternary ammonium salts, and a metal ion exchange reagent comprising silver sodium zirconium phosphate, silver zeolite, or silver ion exchange resin.

4. The fluid container of claim 1 wherein said antimicrobial agent comprises a metal ion selected from one of the following:
 silver;
 copper;
 gold;
 nickel;
 tin; and
 zinc.

5. The fluid container of claim 1 wherein said antimicrobial agent comprises an antimicrobial active material selected from benzoic acid, sorbic acid, nisin, thymol, allicin, peroxides, imazalil, triclosan, benomyl, metal-ion release agents, metal colloids, anhydrides, and organic quaternary ammonium salts.

6. The fluid container of claim 1 wherein said metal-ion sequestering agent has a stability constant greater than $10^{20}$ with iron (III) and said antimicrobial agent comprises a metal ion selected from one of the following:
 silver;
 copper;
 gold;
 nickel;
 tin; or
 zinc.

7. The fluid container of claim 1 wherein said sequestering agent has a high-affinity for biologically important metal ions comprising Mn, Mg, Zn, Cu, and Fe.

8. The fluid container of claim 1 wherein said sequestering agent is immobilized on the surface(s) of said container and has a high-selectivity for biologically important metal ions comprising Mn, Mg, Zn, Cu, and Fe.

9. The fluid container of claim 1 wherein said certain metal ions comprises Mn, Mg, Zn, Cu, and Fe and said other at least one ion comprises calcium.

10. The fluid container of claim 1 wherein said container comprises a bottle.

11. The fluid container of claim 10 wherein said bottle is made of a plastic material.

12. The fluid container of claim 1 wherein said liquid nutrient comprises a beverage.

13. The fluid container of claim 1 wherein said container is in the form of one of the following:
 metal can;
 drink box;
 drink pouch;
 foil wrap;
 glass container; and
 plastic container.

14. The fluid container of claim 1 wherein said sequestering agent and said antimicrobial agent are applied to the interior surface of said container.

15. The fluid container of claim 1 wherein said prescribed condition comprises maintaining said microbes in a biostatic state.

16. The fluid container of claim 1 wherein said prescribed condition comprises maintaining said microbes in a substantially biocide state.

17. The fluid container of claim 1 wherein said prescribed condition comprises maintaining said microbes to a prescribed level.

18. The fluid container of claim 1 wherein said prescribed condition comprises maintaining said microbes to a level that will not harm users.

19. A fluid container for containing a liquid nutrient having a pH equal to or greater than about 2.5, said container having an interior surface having a metal-ion sequestering agent provided in a localized area of the container formed by a two shot molding, insert molding or two shot injection stretch blow molding process, said metal ion sequestering agent provided for removing a designated metal ion from said liquid nutrient for inhibiting growth of microbes in said liquid nutrient and an antimicrobial agent for at least maintaining an amount of microbes in said liquid nutrient to a prescribed condition, wherein said metal-ion sequestering agent comprises derivatized nanoparticles comprising inorganic nanoparticles having an attached metal-ion sequestrant, and wherein said metal-ion sequestrant is attached to the nanoparticles by reacting the nanoparticles with a silicon alkoxide intermediate of the sequestrant having the general formula:

$Si(OR)_{4-x} R'_x$;

wherein x is an integer from 1 to 3;

R is an alkyl group; and

R' is an organic group containing an alpha amino carboxylate, a hydroxamate, or a catechol.

20. The fluid container of claim 19 wherein said metal-ion sequestering agent is immobilized on the interior surface of said container and has a stability constant greater than $10^{10}$ with iron (III).

21. The fluid container of claim 19 wherein said antimicrobial agent comprises an antimicrobial active material selected from benzoic acid, sorbic acid, nisin, thymol, allicin, peroxides, imazalil, triclosan, benomyl, metal-ion release agents, metal colloids, anhydrides, and organic quaternary ammonium salts, and a metal ion exchange reagent comprising silver sodium zirconium phosphate, silver zeolite, or silver ion exchange resin.

22. The fluid container of claim 19 wherein said antimicrobial agent comprises a metal ion selected from one of the following:

silver;
copper;
gold;
nickel;
tin; and
zinc.

23. The fluid container of claim 19 wherein said metal-ion sequestering agent is immobilized on the surface(s) of said container and has a stability constant greater than $10^{10}$ with iron (III) and said antimicrobial agent comprises an antimicrobial active material selected from benzoic acid, sorbic acid, nisin, thymol, allicin, peroxides, imazalil, triclosan, benomyl, metal-ion release agents, metal colloids, anhydrides, and organic quaternary ammonium salts.

24. The fluid container of claim 19 wherein said metal-ion sequestering agent is immobilized on the surface(s) of said container and has a stability constant greater than $10^{10}$ with iron (III) and said antimicrobial agent comprises a metal ion selected from one of the following:

silver;
copper;
gold;
nickel;
tin; and
zinc.

25. The fluid container of claim 19 wherein said sequestering agent is immobilized on the surface(s) of said container and has a high-affinity for biologically important metal ions comprising Mn, Mg, Zn, Cu, and Fe.

26. The fluid container of claim 19 wherein said sequestering agent is immobilized on the surface(s) of said container and has a high selectivity for biologically important metal ions comprising Mn, Mg, Zn, Cu, and Fe.

27. The fluid container of claim 19 wherein said sequestering agent has a high selectivity for certain metal ions but a low-affinity for at least one other ion.

28. The fluid container of claim 27 wherein said certain metal ions comprises Mn, Mg, Zn, Cu and Fe and said other at least one ion comprises calcium.

29. The fluid container of claim 19 wherein said inorganic nanoparticles have an average particle size of less than 200 nm and the derivatized nanoparticles have a stability constant greater than $10^{10}$ with iron (III).

30. The fluid container of claim 19 wherein said container comprises a bottle.

31. The fluid container of claim 30 wherein said bottle is made of a plastic material.

32. The fluid container of claim 19 wherein said liquid nutrient comprises a beverage.

33. The fluid container of claim 19 wherein said container is in the form of one of the following:

a metal can;

a drink box;

a drink pouch;

a foil wrap;

a glass container; and a plastic container.

34. The fluid container of claim 19 wherein said sequestering agent and said antimicrobial agent are applied to the interior surface of said container.

35. The fluid container of claim 19 wherein said prescribed condition comprises maintaining said microbes in a biostatic state.

36. The fluid container of claim 19 wherein said prescribed condition comprises maintaining said microbes in a substantially biocide state.

37. The fluid container of claim 19 wherein said prescribed condition comprises maintaining said microbes to a prescribed level.

38. The fluid container of claim 19 wherein said prescribed condition comprises maintaining said microbes to a level that will not harm users.

* * * * *